(12) United States Patent
Dovichi et al.

(10) Patent No.: US 11,746,388 B2
(45) Date of Patent: Sep. 5, 2023

(54) SYSTEMS AND METHOD FOR ELECTROPHORETIC FRACTIONATION OF THE MICROBIOME

(71) Applicant: University of Notre Dame du Lac, South Bend, IN (US)

(72) Inventors: Norman Dovichi, South Bend, IN (US); Bonnie Jaskowski Huge, South Bend, IN (US); Matthew Champion, South Bend, IN (US)

(73) Assignee: University of Notre Dame Du Lac, South Bend, IN (US)

( * ) Notice: Subject to any disclaimer, the term of this patent is extended or adjusted under 35 U.S.C. 154(b) by 546 days.

(21) Appl. No.: 16/987,093

(22) Filed: Aug. 6, 2020

(65) Prior Publication Data

US 2020/0385787 A1 Dec. 10, 2020

Related U.S. Application Data

(63) Continuation-in-part of application No. 15/914,592, filed on Mar. 7, 2018, now abandoned.

(60) Provisional application No. 62/467,875, filed on Mar. 7, 2017.

(51) Int. Cl.
  *C12Q 1/689* (2018.01)
  *G01N 27/327* (2006.01)
  *C12Q 1/686* (2018.01)

(52) U.S. Cl.
  CPC ............. *C12Q 1/689* (2013.01); *C12Q 1/686* (2013.01); *G01N 27/3273* (2013.01)

(58) Field of Classification Search
  CPC ........ C12Q 1/689; C12Q 1/686; C12Q 1/701; C12Q 1/24; G01N 27/3273; C12N 13/00
  See application file for complete search history.

(56) References Cited

U.S. PATENT DOCUMENTS

| 5,578,460 A | 11/1996 | Ebersole et al. |
| 2011/0220508 A1* | 9/2011 | Liu .................. G01N 27/44743 204/603 |
| 2015/0125883 A1 | 5/2015 | Gordon et al. |

OTHER PUBLICATIONS

Huang et al, Continuous sample collection in capillary zone electrophoresis by coupling the outlet of a capillary to a moving surface, 1990, Journal of Chromatography, 516, 185-189. (Year: 1990).*
Buszewski et al., "Separation of Bacteria by Capillary Electrophoresis," J Sep Sci., 26(11):1045-1049, Jul. 2003.
Ebersole et al., "Separation and Isolation of Viable Bacteria by Capillary Zone Electrophoresis," Nat Biotechnol., 11:1278-1282, Nov. 1993.
Jaskowski Huge et al., "Capillary Electrophoresis Coupled with Automated Fraction Collection," Talanta, 130:288-293, Dec. 2014.
Krylov et al., "Instrumentation for Chemical Cytometry," Anal Chem., 72(4):872-877, Jan. 2000.
Vannatta et al., "CE-MALDI Interface Based on Inkjet Technology," Electrophoresis, 30(23):4071-4074, Dec. 2009.
Zhu et al., "Simplified Capillary Isoelectric Focusing with Chemical Mobilization for Intact Protein Analysis," J Sep Sci., 40(4):948-953, Feb. 2017.

* cited by examiner

*Primary Examiner* — Narayan K Bhat
(74) *Attorney, Agent, or Firm* — Haukaas Fortius PLLC; Michael Haukaas

(57) ABSTRACT

A system and methods of characterizing a population of a virus, bacteriophage, or other microbes in a microbiome that includes the steps of separating a sample of microbiota into more than one fraction by continuous capillary zone electrophoresis based on the physiochemical properties of the microbes in the microbiota using a constant voltage applied to the sample during the continuous zone electrophoresis. At least one separated fraction includes an intact virus, bacteriophage, or other microbe that may be visualized and/or directly sequenced to characterize the population of the virus, bacteriophage, or other microbe in the microbiome.

9 Claims, 15 Drawing Sheets

Specification includes a Sequence Listing.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
agagtttgat cctggctcag                                               20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
acggctacct tgttacgact t                                             21
```

SYSTEMS AND METHOD FOR ELECTROPHORETIC FRACTIONATION OF THE MICROBIOME

RELATED APPLICATIONS

This application is a continuation-in-part of U.S. patent application Ser. No. 15/914,592 filed Mar. 7, 2018, which claims priority under 35 U. S. C § 119(e) to U.S. Provisional Patent Application No. 62/467,875 filed Mar. 7, 2017, each of which applications are incorporated herein by reference.

REFERENCE TO SEQUENCE LISTING

The present application includes a Sequence Listing submitted electronically in ASCII format and is hereby incorporated by reference in its entirety. Said ASCII copy, created on Apr. 17, 2023, is named 501-075US1_SL_ST25 and is 719 bytes in size.

BACKGROUND OF THE INVENTION

The size of the world's microbiota population is a daunting number. The number of bacteria alone has been estimated by University of Georgia researchers to be around $5 \times 10^{30}$. Other cells such as viruses, archaea, and protists, which are equally as prolific and taxonomically challenging, also make up the microbiota, further increasing the genetic diversity and the information a sample may contain. Recent projects such as the Human Microbiome Project and the Earth Microbiome Project have taken on the herculean task of characterizing microorganisms found in and on these respective domains for the purpose of learning what members and associations are present.

The extreme complexity of environmental microbiomes presents formidable challenges to their characterization by even advanced technologies for sequencing the meta-genomes, such as next-generation sequencing (NGS). Highly abundant species dominate the sequencing data, and huge numbers of sequences must be generated to identify rare species. The deep survey of species present at low levels in a microbiome is challenging using conventional NGS. A small sample may contain thousands of bacteria belonging to diverse genetic groups. A comprehensive characterization of the species present in a sample is difficult even with current high throughput techniques.

Only a small fraction of a microbiota is culturable, and most microbial species are invisible to classic microbiological methods. Microbiota are instead characterized by analysis of their microbiome, which is the corresponding genetic content of those organisms, and includes phylogenetic markers, such as 16S rRNA or HSP60. For marker-based experiments, PCR amplifies a region of the marker, generating sequencing templates. Each template derives from a single bacterium, and that bacterium is characterized based on its marker's sequence. Marker sequences that differ by less than a fixed dissimilarity threshold (often 3%) are clustered. The consensus sequence of each cluster, called an operational taxonomic unit (OTU), is used to classify the microbe by species, genus, or higher taxonomic level. In closed-reference methods, reads similar to a reference database are incorporated into the OTUs.

There are limitations to this approach. Species with similar marker sequences can be combined into a single OTU, obscuring the microbiota's diversity. Sequencing errors can generate spurious OTUs. Rarefication of data inevitably loses information on low abundance species. Sequences that do not map into databases are ignored in closed-reference analyses. However, the most important limitation is that high abundance species generate the majority of OTUs, and a very large number of highly redundant sequences must be generated to detect the sequence from rare species.

Characterization of the microbiota is a sampling process, where the parent population is the entire microbiota in the environment. A laboratory sample is taken from the environment, and a subsample of that laboratory sample is subjected to next-generation sequencing. Each sequence is obtained from a single bacterium, and that process is destructive. As a result, microbiota sequencing is a sampling experiment without replacement, which is characterized by the hypergeometric distribution.

For example, in a case where there are two species in the subsample used in a sequencing experiment, where the abundant species is represented by 105 bacteria, and where 10 bacteria are present from the rare species. 67,000 sequences (67% of the population) must be sequenced to have a 50% chance of detecting an OTU corresponding to the rare species. Of those 67,000 sequences, an average of 66,999 sequences can be from the abundant species and one sequence can be from the rare species. Identification of rare species is inherently inefficient. However, these rare species can play important environmental roles.

Therefore, characterization of a minority of certain microbiota in complex mixtures of more abundant microbiota is difficult or impractical with existing methods. Accordingly, a quicker method that has less oversampling is required in order to efficiently and effectively assesses the composition of the microbiota.

SUMMARY OF THE INVENTION

This disclosure relates to the field of microbiome characterization. In particular, separation of sample components based on their physiochemical properties can aid in identification of species present.

As used herein, an attempt has been made to use the term "microbiota" to indicate the collections of organisms inhabiting a site, whereas the term "microbiome" is used to indicate the genetic information available in a sample containing microorganisms. The microbiome is a characterization of microorganisms in an environment through the corresponding genetic content of those organisms, and includes phylogenetic markers, such as 16S rRNA or HSP60. The microbiota may comprise various bacteria, protists, archaea, viruses, and fungi.

The invention disclosed herein provides for fractionation based on the physiochemical properties of the constituent organisms to provide deeper analysis of the microbiome. If the subsample in the preceding example was separated into two fractions, each containing a single species, then two sequences would be required to identify the species making up this microbiome. Analysis of fractionated sample therefore facilitates identification of rare species.

Capillary zone electrophoresis is used to separate the microbiome into fractions on a suitable collection device such as a microtiter plate. Electrophoresis separates microbes based on their physicochemical properties, and rare species are segregated from highly abundant species. In example, the contents of each microtiter plate well can then be sequenced using 16S rRNA as a phylogenetic marker. Over 2.5 times more operational taxonomic units are generated from the fractionated sample compared to the unfractionated microbiome.

Accordingly, this disclosure provides a device to analyze a microbiome comprising:
- a separation capillary for microbiota having both a distal and a proximal end, wherein the proximal end of the capillary is in fluidic connection with an injection block that is configured for a sample of microbiota;
- a power source that can supply a voltage across the separation capillary;
- a dispensing valve in fluidic connection to a deposition buffer container;
- a nozzle in fluidic connection to the dispensing valve and the distal end of the capillary through a tee fitting;
- a fraction collector comprising a collector plate connected to a movable stage that is below an open end of the nozzle when collecting fractions; and
- a nucleic acid sequencer interfaced with the fraction collector;

wherein a sample of microbiota can be separated by the separation capillary and deposited from the separation capillary in isolation from preceding and succeeding microbiota, and the microbiome of the separated microbiota is analyzed by the sequencer.

This disclosure also provides a method of analyzing a microbiome with the device described above, comprising:
a) inserting a sample comprising a mixture of microbiota into the injection block;
b) applying a voltage to the separation capillary;
c) pressurizing the deposition buffer container, wherein the deposition buffer container comprises a deposition buffer;
d) opening the dispensing valve;
e) collecting fractions of purified microbiota that have been separated from other microbiota in the mixture;
f) optionally amplifying the purified microbiota; and
g) sequencing the nucleic acid of the purified microbiota;

wherein a microbiome within a fraction is analyzed from purified microbiota by nucleic acid sequencing.

The disclosure provides also a method of characterizing the population of a microbiome comprising, separating a sample of microbiota into more than one fractions by capillary zone electrophoresis based on the physiochemical properties of the microorganisms within the microbiota, wherein at least one fraction comprises an intact microorganism, and sequencing the genetic information in at least one fraction, thereby characterizing the population of a microbiome.

In certain embodiments, the intact microorganism is non-culturable.

Certain preferred methods of analyzing a population of a microbiome includes depositing each fraction of the sample separated using the continuous zone electrophoresis into a receptacle for further genetic or biochemical analysis. For example, fractions may be deposited into a microtiter plate and the genetic material from each of those fractions may be sequenced. Advantageously, this method eliminates the requirement of culturing the microbe (e.g., virus or bacteriophage particles, bacteria, etc.) in each separated fraction since a vast majority of such microbes are uncultaruable in a laboratory setting.

According to another preferred embodiment, the disclosure provides a method of analyzing a virus or bacteriophage microbiome comprising:
a) providing a device comprising:
- a separation capillary for an intact virus or bacteriophage microbiota having both a distal and a proximal end, wherein the proximal end of the capillary is in fluidic connection with an injection block that is configured for a sample of the intact virus or bacteriophage microbiota;
- a power source configured to supply a voltage across the separation capillary;
- a background buffer comprising one or more electrolytes wherein the background buffer includes a pH of about 3 to about 11;
- a dispensing valve in fluidic connection to a deposition buffer container;
- a nozzle in fluidic connection to the dispensing valve and the distal end of the capillary through a tee fitting;
- a fraction collector comprising a collector plate connected to a movable stage that is below an open end of the nozzle when collecting fractions; and
- a nucleic acid sequencer interfaced with the fraction collector;

wherein the sample of intact virus or bacteriophage microbiota is separated by the separation capillary;
b) inserting a sample comprising a mixture of virus or bacteriophage microbiota into the injection block;
c) applying a constant voltage to the separation capillary to separate the sample into fractions;
d) pressurizing the deposition buffer container, wherein the deposition buffer container comprises a deposition buffer;
e) opening the dispensing valve;
f) collecting the fractions of purified intact virus or bacteriophage microbiota that have been separated from other microbiota in the mixture;
g) visualizing the fractionated virus or bacteriophage via electron microscopy; and
h) sequencing nucleic acid of the fractionated virus or bacteriophage using the nucleic acid sequencer;

wherein a microbiome within a fraction is analyzed from the fractionated virus or bacteriophage microbiota by nucleic acid sequencing.

One preferred method of characterizing a population of a virus or a bacteriophage in a microbiome comprising, separating a sample of microbiota comprising of the virus or the bacteriophage into more than one fraction by continuous capillary zone electrophoresis based on the physiochemical properties of the virus or the bacteriophage within the microbiota, wherein a constant voltage is applied to the sample during the continuous zone electrophoresis, and wherein at least one fraction comprises an intact virus or bacteriophage, and sequencing the genetic information in at least one fraction, thereby characterizing the population of the virus or the bacteriophage in the microbiome. In certain embodiments, the intact virus or bacteriophage is non-culturable.

A preferred method of analyzing a virus or bacteriophage microbiome includes the use of borate as the background buffer present at a concentration of about 10 mM to about 100 mM, about 10 mM to about 50 mM, about 15 mM to about 35 mM, or more preferably, of about 25 mM, and a voltage applied to the separation capillary of about 250 V/cm to about 350 V/cm, or more preferably, about 300 V/cm. Preferably, the pH of the background buffer is about 8.3.

Certain preferred methods of analyzing a virus or bacteriophage microbiome includes depositing each fraction of the sample separated using the continuous zone electrophoresis into a receptacle for further genetic or biochemical analysis. For example, fractions may be deposited into a microtiter plate and the genetic material from each of those fractions may be sequenced. Advantageously, this method eliminates the requirement of culturing the virus or bacteriophage in each separated fraction since a vast majority of such microbes are unculturable in a laboratory setting.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF THE INVENTION

Figure 1:
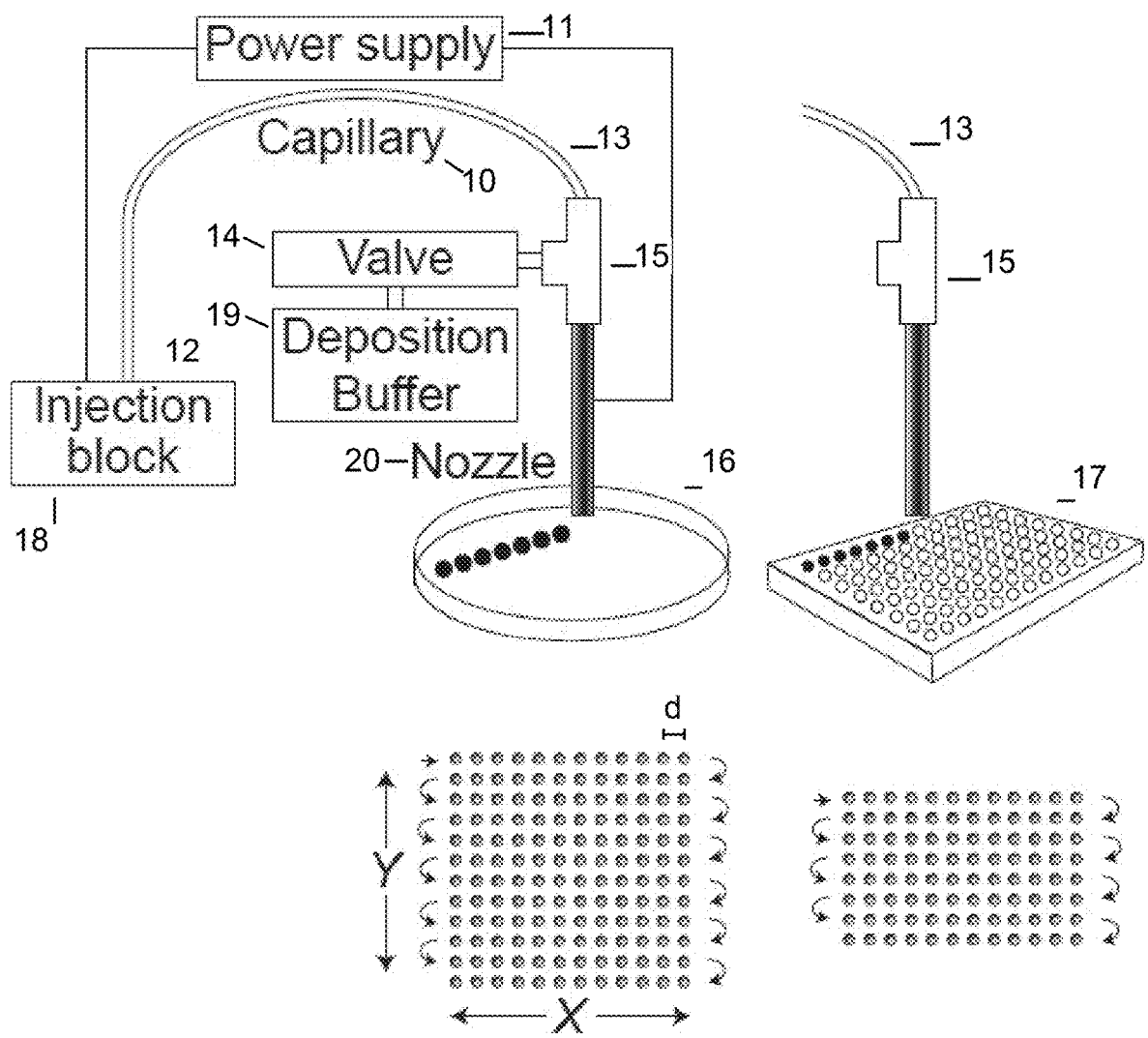
FIG. 1. A schematic of the continuous capillary zone electrophoresis instrument with a fraction collector. The distal end of the separation capillary is threaded through a T-fitting and terminates near the exit of the nozzle. Sheath buffer is pressurized with nitrogen gas. Buffer flow is controlled with the dispensing valve to generate a drop that ensheaths the material exiting the capillary, depositing a drop onto either a Petri dish for microbial growth or into wells of a microtiter plate for genomic analysis. The receiving vessel is mounted on a motorized microscope stage, which is programmed using Labview to move in a serpentine path.

Microbiome analysis benefits from segregation of rare species from highly abundant species. Disclosed herein is the coupling of capillary zone electrophoresis with a sterile fraction collector to separate and characterize a microbiome. In one embodiment, fractions were deposited onto a Petri dish for characterization of culturable microbes and in a different embodiment fractions were collected into wells of a microtiter plate for next-generation sequencing. While some wells of the microtiter plate were dominated by a small number of species, most fractions generated diverse species representation. Analysis of the fractionated microbiome generated 660 operational taxonomic units (OTUs) that mapped to known species, compared with 228 OTUs from the unfractionated sample. One well of the fractionated sample generated 419 OTUs, which is 66% larger than from the unfractionated sample; fractionation moved highly abundant species into different wells of the microtiter plate, allowing identification of rarer species.

There are several methods available for microbiota fractionation. Field flow fractionation separates particles based on their size and diffusivity. Hydrodynamic chromatography separates particles based on their diameter. Liquid chromatography has been used for the separation of phage based on interaction with a stationary phase. Dielectrophoresis has been used for the concentration and separation of simple bacterial mixtures.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%. For example, repeat unit A is substantially soluble (e.g., greater than about 95% or greater than about 99%) in a polar organic solvent and is substantially insoluble (e.g., less than about 5% or less than about 1%) in a fluorocarbon solvent. In another example, repeat unit B is substantially soluble (e.g., greater than about 95% or greater than about 99%) in a fluorocarbon solvent and is substantially insoluble (e.g., less than about 5% or less than about 1%) in a polar organic solvent.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone or two or more of them may be mixed for use to provide a "solvent system".

The term "microbiota" generally refers to an ecological community of commensal, symbiotic and pathogenic microorganisms found in and on all multicellular organisms from plants to animals. A microbiota includes bacteria, archaea, protists, fungi, and viruses. The term "microbiome" generally describes either the collective genomes of the microorganisms that reside in an environmental niche or the microorganisms themselves.

The term "intact" as used herein refers to a cell or particle with structural integrity. Discontinuous electrophoresis may create stress on/in the cell or particle due to a series of voltage drops and ramps while sample remains on-line. Such stress can lyse the cell, which destroys the cellular integrity. The genetic material from lysed cells may be capable of being amplified, but genetic material separated from the cellular content is very difficult to separate via electrophoreses. Instead, an intact cell retains intact the genetic material DNA/RNA contained within for recovery and sequencing, and the physicochemical properties of intact cells allows cells from different species to be separated. Accordingly, in certain preferred embodiments, continuous zone electrophoresis is used in instead of discontinuous zone electrophoresis.

EMBODIMENTS OF THE INVENTION

Figure 8:
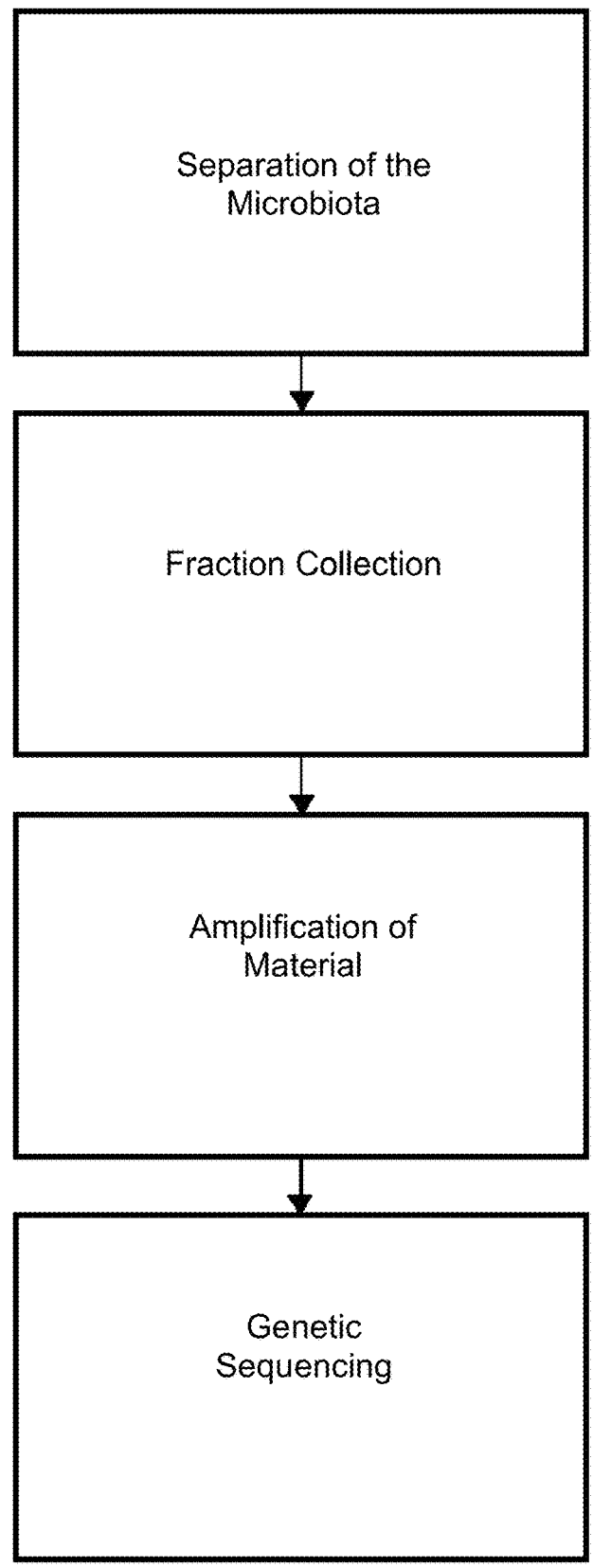
FIG. 8. A flow chart of microbiome analysis, according to an embodiment. Amplification of genetic material is not required, though included here to support the data presented.

Herein is described various embodiments wherein microbiota or the organisms that form the microbiota are introduced into an analyzer through an injection port for analysis (FIG. 8). The microbiota may be in a carrier such as a buffer. The buffer and other solvents that may be present carry the microbiota through a separation capillary that has an internal diameter that is sufficiently large enough to let the microorganisms traverse the capillary and allow for the microbiota or microorganisms to be separated based on their physiochemical properties, and thereby producing purified microbiota or microorganisms as they exit the other end of the capillary. The microbiota traverses the capillary with or without pressure applied to one end of the capillary, or such as the end closest to the injection port. Or the microbiota traverses the capillary that has a voltage applied across the capillary. As the microbiota leave the capillary, the microbiota is substantially grouped according to their type (i.e., purified). The purified microbiota is then mixed with a deposition buffer and passed through a nozzle where droplets comprising the purified microbiota are deposited into or onto a collector. The deposited aliquot may be a drop on a surface such as agar or other growth media, or an aliquot may be deposited to a well-shaped container that may have other media in the well. These collected fractions or selected fractions of purified microbiota can then be manually or automatically transferred to an apparatus for other means of manipulation or analysis, e.g. cell amplification or genetic amplification. Because the microbiota is purified, less signal noise is introduced during the amplification process so that the minor microbiota or microorganism that were present in the original sample are more easily amplified and detected during later stages of analysis. After amplification, the cells or genetic material are then sequenced where the fainter signals can now be better detected with less confounding noise from the background signal. Thus, the data manipulation has the potential for greater bandwidth, dynamic range, precision, fidelity, or a combination thereof.

FIG. 8 represents the sequence of steps for an apparatus to provide genetic sequencing of microorganisms that are, for example, in a minority in a sample of microbiota. The sequence of steps are as follows: 1) Separation of microbiota; 2) Fraction collection; 3) Amplification of cells or genetic material in a cell if necessary; and 4) Genetic sequencing. Preferred embodiments omit the amplification of the fractionated cells or genetic material prior to genetic sequencing. This disclosure encompasses all means that are currently available or will be available for performing the four steps in the sequence disclosed. Preferred embodiments are discussed throughout this disclosure, such as using CZE for separating microbiota, but other embodiments can be envisioned as part of the disclosed invention. The steps can be performed manually, semi-automatically, or fully automatically. The "eluent" (e.g., purified microbiota) dispensed from a separation capillary (via an open orifice at one end of the nozzle) can be transferred automatically to the next unit in the disclosed apparatus that performs the sequence 1-4, described above.

Accordingly, this disclosure describes various embodiments of a device to analyze a microbiome comprising:
  a separation capillary for microbiota having both a distal and a proximal end, wherein the proximal end of the capillary is in fluidic connection with an injection block that is configured for a sample of microbiota;
  a power source that can supply a voltage across the separation capillary;
  a dispensing valve in fluidic connection to a deposition buffer container;
  a nozzle in fluidic connection to the dispensing valve and the distal end of the capillary through a tee fitting;
  a fraction collector comprising a collector plate connected to a movable stage that is below an open end of the nozzle when collecting fractions; and
  a nucleic acid sequencer interfaced with the fraction collector;
  wherein a sample of microbiota can be separated by the separation capillary, and the microbiome of the separated microbiota is analyzed by the sequencer.

In additional embodiments, the fraction collector can be a platform that is substantially planar for receiving deposited fluids, or the fraction collector comprises wells to hold fluids for another step in an analysis or long-term storage. In some embodiments, the fraction collector can move relative to the open end of the nozzle to a new position when each new fraction is collected. In some embodiments, the device comprises an autosampler, a polymerase chain reaction apparatus, or a combination thereof. In some embodiments, the separation capillary is configured for a voltage of about 50 V/cm to about 1000 V/cm for capillary zone electrophoresis. In some embodiments, the separation capillary has an inner diameter of about 1 µm to about 500 µm. In other embodiments the inner diameter of the capillary is about 0.01 µm to about 0.1 µm, about 0.1 µm to about 0.5 µm, about 0.5 µm to about 1 µm, about 1 µm to about 10 µm, about 5 µm to about 50 µm, about 50 µm to about 100 µm, about 100 µm to about 200 µm, about 200 µm to about 300 µm, about 300 µm to about 400 µm, about 400 µm to about 500 µm, or about 500 µm to about 750 µm.

Additionally, this disclosure provides a method of analyzing a microbiome with the apparatus disclosed above, comprising:
a) inserting a sample comprising a mixture of microbiota into the injection block;
b) applying a voltage to the separation capillary;
c) pressurizing the deposition buffer container, wherein the deposition buffer container comprises a deposition buffer;
d) opening the dispensing valve;
e) collecting fractions of purified microbiota that have been separated from other microbiota in the mixture;
f) optionally amplifying the purified microbiota; and
g) sequencing the nucleic acid of the purified microbiota;
wherein a microbiome within a fraction is analyzed from the purified microbiota by nucleic acid sequencing.

In some embodiments, the dispensing valve opens when fractions are collected. In some embodiments, the injection block comprises the sample and a sample buffer. In some embodiments, the sample buffer and the deposition buffer are chemically similar. In some embodiments, the fraction collector comprises a microtiter plate, a Petri dish, or a combination thereof. In some embodiments, the Petri dish comprises a cell growth medium. In some embodiments, the microtiter plate comprises a series of wells, and wherein at least one well comprises a lysis reagent mix for conducting a polymerase chain reaction.

This disclosure also provides a method of characterizing the population of a microbiome comprising, separating a sample of microbiota into more than one fraction by capillary zone electrophoresis based on the physiochemical properties of the microorganisms within the microbiota, wherein at least one fraction comprises an intact microorganism, and sequencing the genetic information in at least one fraction, thereby characterizing the population of a microbiome.

In some embodiments, the sample is separated through a separation capillary having an inner diameter of about 1 µm to about 300 µm and a voltage of about 50 V/cm to about 500 V/cm. In other embodiments throughout this disclosure, the voltage for capillary zone electrophoresis (CZE) is about 1 V/cm to about 1000 V/cm, about 1 V/cm to about 100 V/cm, about 100 V/cm to about 200 V/cm, about 200 V/cm to about 300 V/cm, about 300 V/cm to about 400 V/cm, about 400 V/cm to about 500 V/cm, or about 500 V/cm to about 750 V/cm. In some embodiments, the fractions are deposited at separate locations on a collection plate.

In one preferred embodiment, the voltage for capillary zone electrophoresis is about 250 V/cm to about 350 V/cm, or about 290 V/cm to about 310 V/cm, and preferably about 300 V/cm.

In some embodiments, the genetic material in at least one fraction is amplified. In some embodiments, the amplification of genetic material occurs by the growth of new cells in a cell growth medium. In some embodiments, the genetic material in at least one fraction is amplified by lysing the cell of a microorganism and conducting a polymerase chain reaction. In some embodiments, the genetic material in at least one fraction is labeled with a unique barcode, and wherein at least one fraction is sequenced to determine the genetic identity of the microorganism present in the one fraction. In some embodiments, the genetic identity of the microorganism present is determined by operational taxonomic units present in at least one fraction.

This disclosure provides ranges, limits, and deviations to variables such as volume, mass, percentages, ratios, etc. It is understood by an ordinary person skilled in the art that a range, such as "number 1" to "number 2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number 10", it implies a continuous range that includes whole numbers and fractional numbers less than number 10, as discussed above. Similarly, if the variable disclosed is a number greater than "number 10", it implies a continuous range that includes whole numbers and fractional numbers greater than number 10. These ranges can be modified by the term "about", whose meaning has been described elsewhere in this disclosure.

Preferred embodiments of capillary zone electrophoresis may include the use of the application of a constant voltage to the separation capillary to separate a sample within the separation capillary into discreet fractions. This is known as continuous capillary zone electrophoresis. Advantageously, continuous capillary zone electrophoresis system permits the continuous separation of analytes such as viruses, bacteriophages, and other microbiota in a sample during electrophoresis. This is achievable, at least in part, because the electric current and voltage applied to the system is ensured by grounding of the dispensing valve with the online buffer system so that the fraction collection instrument achieves uninterrupted separation of the sample while simultaneously depositing the separated fractions of the sample from the capillary into a vessel for downstream analysis. This also provides a high level of reproducibility and facilitates an in line continuous fraction collection, deposition without removing voltage.

Results and Discussion

Embodiments of the invention disclosed herein are directed to the electrophoretic fractionation of bacteria. A rich literature developed in the 20th century that studied the electrophoretic behavior of bacteria, and instrumentation was commercialized for measurement of electrophoretic mobility and zeta potential of microbes.

Conventional electrophoresis is cumbersome, whereas capillary electrophoresis is much more easily automated for large-scale projects, including the sequencing of the human genome. Ebersole and McCormick performed a pioneering study that employed capillary zone electrophoresis (CZE) for the separation of two pure bacterial cultures. Fractions were manually collected and were of high purity and retained high bacterial viability. Armstrong and others followed this work with a number of publications that characterized relatively simple bacterial mixtures using CZE. These early studies suffered from two limitations. First, manual manipulations were required to collect fractions. Second, simple methods were used to characterize the fractionated bacteria.

The invention disclosed herein is directed to an automated capillary electrophoresis fraction collector. There are related publications of this system to couple CZE with MALDI mass spectrometry and for isolation of oligonucleotides bound to proteins for generation of aptamers. Described herein is CZE with this fractionator for analysis of a complex environmental microbiome. Fractions are deposited onto a Petri dish to study culturable organisms or into wells of a microtiter plate for next-generation sequencing. One skilled in the art can consider additional microbiota separation means.

Comprehensive identification of microorganisms in the microbiota is aided by separating the organisms present into fractions of reduced complexity. Environmental microbiota samples contain an unknown number of organisms in an unknown number of taxonomic categories. Separation of the microbiota can be accomplished through the physio-chemical properties of the organisms that are present. The organisms present, such as bacteria, can be separated through the use of electrophoresis where a voltage is applied across a capillary. The environmental sample is introduced to the proximal end of the capillary. In one embodiment of the invention the capillary is an uncoated silica capillary. In another embodiment, the capillary may be coated to aide in the separation of particular constituents. In another embodiment, reagents can be added to the separation electrolyte to modify the separation. The applied voltage can cause microbial species of different size and charge to travel at different rates along the capillary.

To segregate the sample, the distal end of the capillary is paired with a nozzle and dispensing valve. The nozzle dispenses the sample onto a collection plate for a period of time. At the completion of this time period the collection plate is moved relative to the nozzle and the sample exiting from the capillary is deposited in a separate location. In this manner, separate fractions of the original sample are segregated.

In one embodiment, the deposition of sample begins with the start of electrophoresis. In another embodiment, a volume approximate to the void volume may be directed to a waste stream or otherwise discarded prior to depositing the sample to be used in further analysis.

The fraction width is the period of time a fraction is deposited in a given location. The fraction width may be equal among all the fractions or may have varying times. Shorter fraction widths may have a finer granularity of the organisms present in the fraction. In one embodiment, the fraction width may be equal across all fractions. The fraction width in this case can be equal to the total separation time, or the time it takes for the entire sample to be eluted from the capillary divided by the number desired fractions. For a given sample window, more fractions can lead to a shorter fraction width. If a particular sample is expected to have organisms with similar separation times, a shorter fraction width during this period may be desired. In one embodiment of this invention the fraction width may be between 0.1 s and 100 s, between 0.5 s and 60 s, between 1 s and 45 s, between 2 s and 40 s, or between 5 s and 30 s.

The collection plate can be mounted on a movable or motorized stage for automated sample collection. The collection plate can be a Petri dish, which contains a cell growth medium or it can be a plate with a series of wells such as a microtiter plate. Fractions collected in a Petri dish may be cultured and processed for genomic sequencing. Fractions collected in the individual wells of a microtiter plate can be lysed in the wells and then amplified by polymerase chain reaction. The DNA in each well can then be molecularly barcoded to identify it as belonging to a specific fraction. Each fraction may be sequenced in parallel according to protocols for techniques such as next generation sequencing. Without ascribing to any particular theory, the preparatory separation of sample fraction prior to sequencing enhances the number of rare species present in the overall sample. Providing each fraction with a unique molecular barcode aids the database facilitated identification of OTUs. It is also within the scope of this invention to sequence just one of the fractions, such as for example, the fraction with the highest number OTUs as calculated according to the PCR threshold value (CT).

An environmental microbiota sample is meant as a broad term referring to real world samples that may be taken from anywhere. These samples include those taken from the natural environment such as the soil, sub-soil, waterways, and air. Environmental samples can also refer to samples from industrial or built environments and include samples from effluent streams, wastewater, or specific collection points in all locations public and private. Environmental samples can also come from, on, or within plants and animals including humans. These samples can further come from biologic fluids, clinical samples, or from specific areas of the body or organ.

As shown in FIG. 1, an uncoated fused silica capillary is used as the separation capillary (10) of a capillary zone electrophoresis instrument for the segregation of the microbiota population in a sample solution. This capillary may be about 100 µm inner diameter (ID), about 160 µm outer diameter (OD), and about 60 cm in length. The ID of the capillary can be varied according to the expected physical characteristic of the individual microorganisms in the microbiota. The inner diameter should not be smaller than the diameter of the largest cell in the microbiota. The ID of the separation capillary may be between 1 to 500 preferably between 20 and 300 and more preferably between 50 and 150 The length of the separation capillary may be between 10 and 200 cm, preferably between 20 and 150 cm and more preferably between 30 and 120 cm. The proximal end of the capillary (12) is inserted into an injection block (18) similar to a published design which was "Instrumentation for Chemical Cytometry" published in *Analytical Chemistry in 2000* (v72, pp 872-8'7'7). The distal end of the capillary was connected to a fraction collector, as described below.

The capillary electrophoresis-fraction collection system is diagramed in FIG. 1. The proximal tip (12) of the capillary was held in an injection block (18). The distal end of the separation capillary (13) was threaded through a Tee fitting (15) using a capillary sleeve and ferrule from Upchurch Scientific (Oak Harbor, Wash. USA). The valve, tee, nozzle, and inline filter are described in further detail in "CE-MALDI interface based on inkjet technology" published in *Electrophoresis* in 2009 (v30, pp 4071-4074) and were from The Lee Company (Westbrook, Conn. USA). The nozzle (20) was secured above a motorized microscope stage (Prior Scientific, Rockland, Mass. USA), which holds a collection plate. The motorized microscope stage can be programmed in Labview (National Instruments, Austin, Tex. USA).

In operation, the electrophoretic background electrolyte and deposition buffer can be matched. In one example, 10 mM Tris-HCl (pH 7.5) served as the background electrolyte. In other embodiments, the background electrolyte is borate. In certain embodiments, the background buffer containing the background electrolyte may have a pH range between 3 and 11. In other embodiments, the background buffer containing the background electrolyte may have a pH of about 7.5 to about 8.5, a pH of about 8 to about 8.5, or a pH of about 8. In some embodiments, the background electrolyte is present at a concentration of about 1 mM to about 100 mM, 10 mM to about 100 mM, about 10 mM to about 50 mM, or about 10 mM to about 25 mM. In one specific embodiment, the background electrolyte is borate present at a concentration of about 25 mM or at 25 mM and the background buffer has a pH of about 8.3 or at 8.3. In some embodiments, the deposition buffer can be held under pneumatic nitrogen pressure at about 3.5 psi and pneumatically injected for 0.5 seconds.

Electrophoresis can be performed at 14 kV which produces a separation voltage of 233 v/cm base on a 60 cm separation capillary where the nozzle was held at ground potential. The voltage was supplied by a Spellman High Voltage power supply (11) (CZE1000R, Newark, N.J. USA). Electrophoresis and fractionation can begin simultaneously. The applied voltage can be varied to achieve the desired separation voltage according to the separation capillary length. In certain embodiments, a continuous voltage of about 250 v/cm to about 350 v/cm is applied to the separation capillary.

There are a number of approaches to improve the separation and contemplated within the scope of the invention disclosed herein. Separations can be manipulated by use of appropriate reagents and pH for the CZE separation. Alternative separation methods include isoelectric focusing. The latter is particularly powerful, and its operation has been simplified, albeit for mass spectrometry detection of separated proteins as is described in "Simplified Capillary Isoelectric Focusing with Chemical Mobilization for Intact Protein Analysis" published in the Journal of Separation Science in 2017 (v40, pp 948-953). Alternatives include liquid chromatography, field-flow fractionation, dielectorphoresis, or any other means that separates microbes based on their physicochemical properties.

A collection plate is secured to the motorized stage, which can be programmed to move a distance d in the X direction n times, where n is equal to the number of fractions per row. Once the nozzle was positioned over the last intended deposition spot in a row, the motorized stage can then move a distance d in the Y direction, and then d in the −X direction by n. In this manner fractions were deposited as the motorized stage moved back and forth under the nozzle. As the nozzle reached the end of a stage the motorized stage can then be moved in the Y direction to place the nozzle over the next row.

Different deposition patterns could be desirable and are within the scope of this application. For example, two programs are diagrammed in FIG. 1. For deposition onto agar plates (16), the motion of the stage can be programmed to match the dimensions of a standard Petri dish with 5 mm spot spacing (d1 and d2 are equal to 5 mm) in the X and Y dimensions in a 12×12 grid (n=12). Fraction width, which controls time between depositions, was set to 9 s. Valve width, which controls the droplet volume, was programmed to dispense 0.35 µL of deposition buffer with each fraction as it exits the capillary. For deposition into microtiter plates, the motion of the stage was programmed to match the dimensions of a standard 96-well plate with 9 mm spot spacing in the X and Y dimensions in an 8×12 grid. Fraction width was set to 15 s. Droplet volume remained 0.35 µL.

Fractionated samples which contain a culturable microbiome population can be collected on Agar plates. Once these separated samples have been fraction collected, they can then be amplified by polymerase chain reaction (PCR). A CFX96 Touch Real-Time pPCR Detection System (Bio-Rad) and universal 16S rRNA primers (ReadyMade Primers, IDT): forward primer 5'-AGA GTT TGA TCC TGG CTC AG (SEQ ID NO: 1), reverse primer 5'-ACG GCT ACC TTG TTA CGA CTT (SEQ ID NO: 2) can be used in the PCR process. The plates are sealed and centrifuged prior to real-time PCR: 95° C. for 3 min followed by 40 cycles of 95° C. for 10 s (denature), 55.8° C. for 20 s (anneal), and 72° C. for 20 s (extend). PCR products are purified (QIAquick PCR Purification Kit, Qiagen) and submitted for Sanger sequencing on an Applied Biosystems 96-capillary 3730xl DNA Analyzer (Genomics & Bioinformatics Core Facility at the University of Notre Dame). The resulting sequences are quality trimmed with 4Peaks software. The sequences were compared and clustered into OTUs using Qiime against the GreenGenes database. Both Qiime and 4Peaks software are available from commercial sources.

In other embodiments of the invention, a fractionated sample can be processed for genomic sequencing through a next-generation sequencing technique. These fractionated samples can be collected on a microtiter plate such as a commonly known 96-well plate. These plates can be prepared with a lysis reagent mix such as the prepGem Bacteria kit. This lysis mix can contain the following reagents per well: 0.15 µL buffer (10×), 0.015 µL prepGem, 0.015 µL lysozyme, 0.82 µL ddH$_2$O).

The plates were prepared for PCR amplification with iTag 16S rRNA V4-V5 primers (Joint Genome Institute) using a real-time system. A suitable PCR protocol includes a 98° C. hold for 3 min followed by 40 cycles of (a) 98° C. for 30 s (denature), (b) 50° C. for 30 s (anneal), and (c) 72° C. for 36 s (extend), and a final extension at 72° C. for 5 min and held at 4° C. until removed. The contents of the wells are subjected to genetic sequencing. This sequencing can target the complete DNA sequence of an organism or a portion thereof. As an example, the fractionated and amplified sample may be sequenced by multiplex paired-end Illumina sequencing of the V4-5 region of bacterial 16S rRNA genes with a MiSeq. Fraction samples on the microtiter 96-well plates are quantified and individual libraries were amplified with single barcode primers according to the sequencing standard operating protocol. Fractionated samples, once amplified, are barcoded in their individual wells can be pooled at up to 184 samples per sequencing run and sequenced on an Illumina MiSeq sequencer in 2×300 run mode.

A sequencing run may return a large amount of sequence data. In once example of a fractionated sample processed according to the process described in the preceding paragraph, about 23,000,000 sequences were returned, each around 300 bp. Quality filtering of raw data is then performed at the using Qiime, as an example. The forward reads can be extracted from each interleaved file, barcode mapped, and closed reference OTU picking can then be performed on each fraction followed by taxonomy assignment using the GreenGenes database.

Advantageously, the embodiments of the devices and methods described herein are designed for electrophoretic fractionation of multi-scale analyte using capillary electrophoresis as a preparative tool for genomic sequencing. The devices and methods specifically aid in analysis and identification of microorganisms that naturally exist within complex microbial communities. No prior knowledge of the microorganisms is necessary for downstream analysis, nor modification of the microorganism from its natural state prior to separation (i.e. primer design for PCR or immunoassay). Further, the resolution of species and strains is reliant on maintaining intact organisms during electrophoresis. Free genetic material will migrate in a discrete band regardless of origin and may only be separated from intact cells or particles as bulk genetic material using this method.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials and Methods

Fused silica capillary was purchased from Polymicro Technologies (Phoenix, Ariz. USA). *Escherichia coli* HB101:pBAD (Amp$^R$) strain expressing GFP was purchased from Bio-Rad (Hercules, Calif. USA). 20% L-arabinose sterile solution was purchased from Teknova (Hollister, Calif. USA). Other reagents were analytical grade and purchased from Sigma-Aldrich (St. Louis, Mo. USA). All solutions were prepared from deionized-distilled water obtained from a Barnstead Nanopure System (Thermo-Fisher Scientific, Waltham, Mass. USA).

All culture-related consumables and glassware were purchased sterile or autoclaved prior to use. Bacteria were cultured using LB medium (Miller's LB powder) supplemented with 100 μg/mL ampicillin in culture tubes at 37° C. at 150 rpm overnight. Fresh LB medium was inoculated with the overnight cultures (1:100 dilution) in shaking flasks and incubated at 37° C. at 150 rpm until they reached a logarithmic phase of growth; 3.5 h total, supplemented with 0.2% L-arabinose at 2 h. Liquid cultures were washed three times with sterile-filtered PBS (Dulbecco's Phosphate Buffered Saline).

Capillaries were conditioned by flushing with MeOH, ddH$_2$O, 1 M NaOH, ddH$_2$O, and 10 mM Tris-HCl in series prior to each analysis. The reservoir and lines supplying deposition buffer to the valve and nozzle were flushed with EtOH, ddH$_2$O, and 10 mM Tris-HCl.

Example 1: *E. coli* Single Species Fractionation

In one example of electrophoretic fractionation and sequencing of a microbiome, *E. coli* cells were diluted in PBS (Phosphate Buffered Saline) for injections of 500 and 5,000 cells, and fractions were deposited onto LB agar supplemented with ampicillin and L-arabinose. Immediately after fractionation, plates were incubated at 37° C. for 15 h. Plates were photographed under a UV lamp after incubation.

A 100 μm ID, 60-cm long uncoated fused silica capillary was used for electrophoresis. Separation was performed at 14 kV. 10 mM Tris-HCl was the background electrolyte. Fractions were deposited in nine-second interval.

Figure 2:
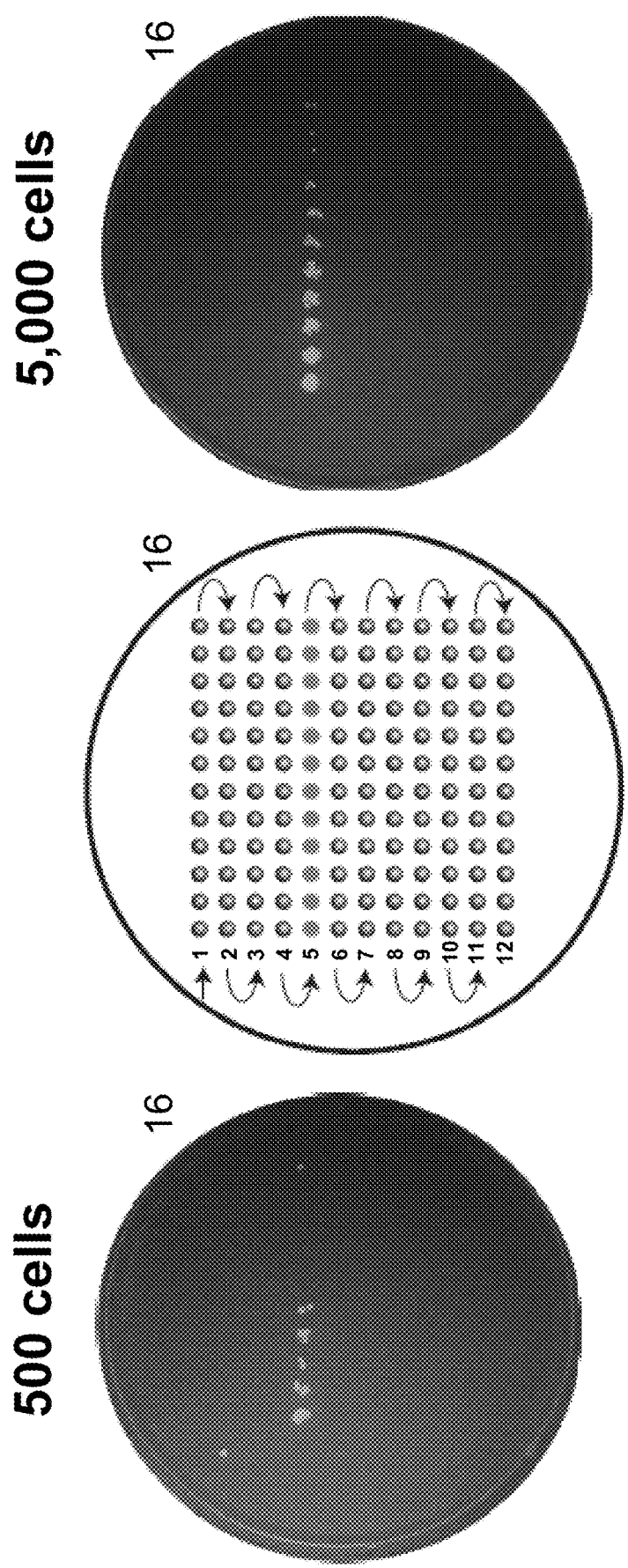
FIG. 2. A fluorescence image of GFP-expressing *E. coli* subjected to capillary electrophoresis, deposition onto a Petri dish, cultured and imaged under UV light illumination. The left image shows the results of an injection of ~500 cells. The middle image shows a cartoon of serpentine deposition pattern. The right image shows an injection of ~5,000 cells.

To visualize the performance of the system for a pure sample, plugs containing ~500 and 5,000 *E. coli* cells were injected into the separation capillary and subjected to electrophoresis. This *E. coli* strain expresses a GFP plasmid. Fractions were deposited a serpentine pattern onto a Petri dish, incubated, and imaged under black-light illumination as seen in FIG. 2. Deposition began with the application of the electric field to the capillary.

In this system, the electropherogram is visualized in FIG. 2 as fluorescent colonies and demonstrates separation of intact organisms. Single colony counting is analogous to single molecule counting in molecular shot-noise limited experiments with fluorescence detection. Single colony counting has limited dynamic range because colonies overlap and merge when several colonies form in a single deposition spot.

Except for one stray colony, no colonies were observed until ~7.5 minutes into the electrophoresis runs of FIG. 2. During migration of this void volume, only sterile solution is deposited. At ~7.5 minutes, a set of fluorescent colonies was formed within the area defined by the deposited drop for injection of 500 and 5,000 cells. The number of colonies per deposition spot appears to decrease roughly exponentially with time, forming a peak with a half-width of approximately nine seconds.

There are at least two causes for the peak tailing. First, the fraction collector may have a dead volume that acts as a well-stirred reactor, producing the exponential tail. Second, the *E. coli* population is heterogeneous in its growth phase, and cells have size distributions, which may lead to differential migration.

Example 2: Wastewater Treatment Plant Microbiome

In another example of electrophoretic fractionation and sequencing of a microbiome, a 2 L aliquot of primary effluent was collected at a wastewater treatment facility. The sampling site was post-settling and pre-chlorination. Microorganisms were isolated by centrifugation and washed three times with sterile-filtered PBS. The washed cells were suspended in PBS supplemented with glycerol (22%) for long-term storage at ~80° C. Aliquots were thawed and dilute in sterile PBS prior to analysis.

The collected sample was divided into multiple subsamples of the wastewater microbiome containing approximately 1,000 and 100,000 microbial cells; these subsamples were injected and separated. Fractionated samples were deposited onto collector plates. These collector plates included those having a cell growth medium such as agar, as well as a microtiter plate. In some instances, the fractionated sample was collected on a plate with LB agar, in triplicate (for 1,000-cell and 100,000-cell injection). Other fractionated samples were deposited on MacConkey agar, in duplicate (for 1,000-cell injection). These plates were incubated at 37° C. for 15 h and photographed. Boilates were prepared from the colonies formed on each of the plates resulting from the 1,000-cell injections: colonies from each fraction were picked and transferred to new LB or MacConkey-agar plates, re-growth was sampled and transferred to 100 μL sterile 1×PBS and heated to 95° C. for 15 minutes to extract genomic DNA. Genomic DNA was clarified by centrifugation at 12,000×g for 5 mins. Another subsample of the wastewater microbiota containing approximately 100,000 microbial cells was injected and separated. The fractionated sample was collected directly into a prepared microtiter plate to facilitate in-well cell lysis. Fraction width was modified to match an approximate separation window of 21 mins (15 s, 7×12 grid) with 12 wells of the 96 well plate reserved for unfractionated controls. The parent sample was reserved, serially diluted in PBS, and added to the remaining 12 wells: 100,000, 20,000, 4,000, and 800 cells/well, in triplicate. The plate was sealed, and samples were incubated to induce cell lysis and DNA extraction (37° C. for 15 mins, 75° C. for 15 mins, 95° C. for 5 mins, and hold at 4° C.). This process was repeated in triplicate.

Figure 3:
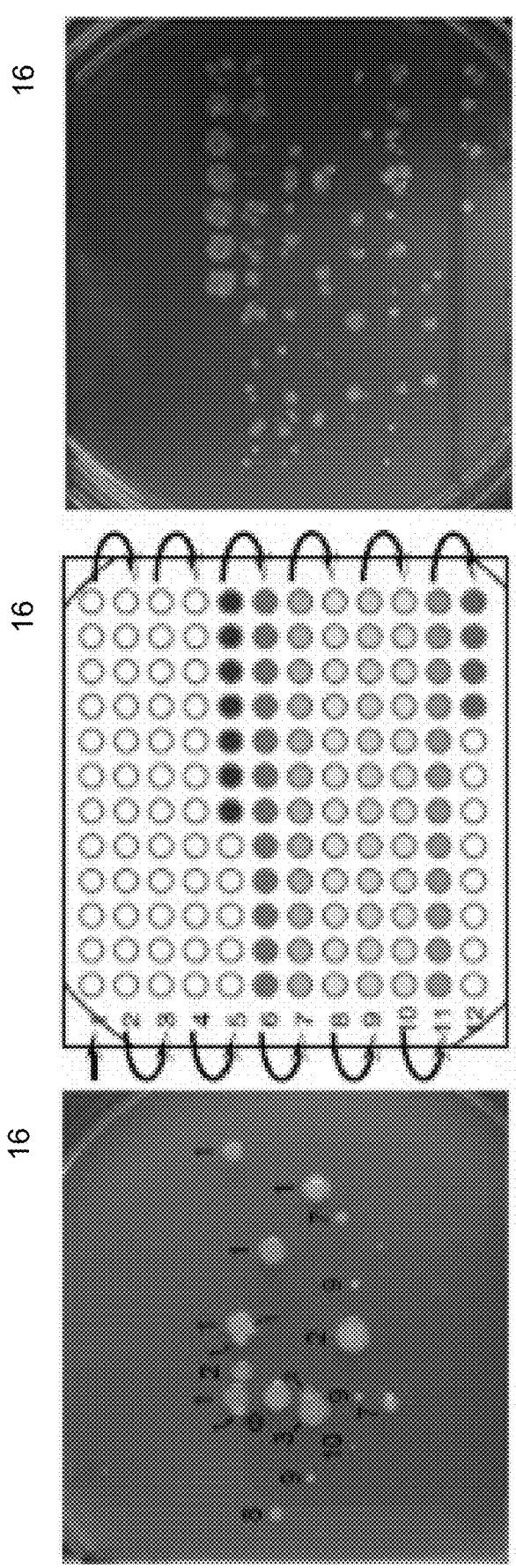
FIG. 3. An image of deposition onto a Petri dish of fractionated microbes from an environmental microbiota after electrophoretic separation and subsequent culture. The left image shows injection of ~1,000 microbes; colonies were cultured, and sequence was generated across the 16S rRNA gene using Sanger sequencing. The middle image shows the deposition path. The right image shows the injection of ~100,000 cells.

The environmental microbiota isolated from the primary effluent of a regional wastewater treatment facility. Roughly 1,000 microbial cells were injected into the capillary. Fractions were deposited on LB plates in triplicate. FIG. 3 left shows the colonies formed after separation, collection, and incubation on one LB plate. Like analysis of E. coli, there is a void volume at the start of the run. A total of ~15 colonies formed in this run, which is consistent with the low culturable rate of environmental microbiota. An injection of ~100,000 cells generated a much more complex plate with a concomitant increase in the number of colonies, as shown on the right image of FIG. 3.

Colonies were samples and plated from the 1,000 cell injections. The 16S rRNA gene was amplified and Sanger sequenced. Paired forward and reverse sequence reads span the entire 16S rRNA gene. All colonies returned sequence data that produced a match in a SSU database with one exception: one colony (SI Mac plate) was not identified due to poor sequence quality in both the forward and reverse directions. The colony marked 0 in FIG. 3 was not bacterial. The gDNA extracted from this region did not amplify and was not sequenced. Both results are omitted from Table 1.

TABLE 1

Culturable Wastewater Taxonomic Summary.

| Bacterial Taxa Summary | Forward Reads (# OTU) | Reverse Reads (# OTU) | Average (# OTU) |
|---|---|---|---|
| Phylum | 2 | 2 | 2 |
| Class | 3 | 3 | 3 |
| Order | 5 | 5 | 5 |
| Family | 5 | 5 | 5 |
| Genus | 20 | 19 | 20 ± 1 |
| Species | 41 | 24 | 33 ± 12 |

The sequences were matched to a microbial SSU database and the results are reported in Table 1 identifying the colonies shown in the left image of FIG. 3. The most common taxa observed were in the Aeromonadaceae or Enterobacteriaceae families. Both are common to the human gut microbiota. The reads in both directions were in agreement at the kingdom, family, and genus levels. At the species level, the forward sequence reads tended to flag more identifications than the reverse. The organism identities presented in supporting information are limited to the taxonomic level at which both reads were in agreement.

Example 3. Generation of a Total Organism Electropherogram (TOE) for an Environmental Microbiome Using Real-Time PCR Roughly 100,000 microbial cells from the waste-water microbiome were injected into the capillary. The microbiome was separated, and fractions were deposited into 80 wells of a microtiter plate. Real-time PCR was used to quantify the number of bacteria within each well. The period between drops was increased to 15 seconds to accommodate separation window of about 20 minutes. Real-time PCR was performed by amplification across the 16S rRNA gene. Amplification was observed for all wells. The Ct values from the PCR reactions were used to estimate the number of bacteria per well. Intensity was calculated according to Equation 1:

$$\text{Intensity} = \text{normalization factor} * 2^{-Ct} \quad \text{(Eq. 1)}$$

where the normalization factor is determined by depositing a known number of E. coli cells into wells. The plot of intensity vs time resembles a conventional electropherogram, in this case where the abundance corresponds to the total number of 16s RNA genes present per well; this plot is named a total organism electropherogram (TOE) by analogy with a total ion electropherogram generated when using mass spectrometry detection in capillary electrophoresis. The TOE provides a visual display of the quality of the separation.

The TOEs were quite reproducible in shape, consisting of a low amplitude signal corresponding to the baseline generated during the void volume, a sharp peak, and a return to an elevated baseline. The main peak was fit with a Gaussian function $(NL*e^{-0.5*(t-t0)2/sigma2})$; the average migration time was 8.5±0.3 min (n=3). The average width of the Gaussian fitting function is 0.1 min, which corresponds to one half of a deposition period.

Figure 4:
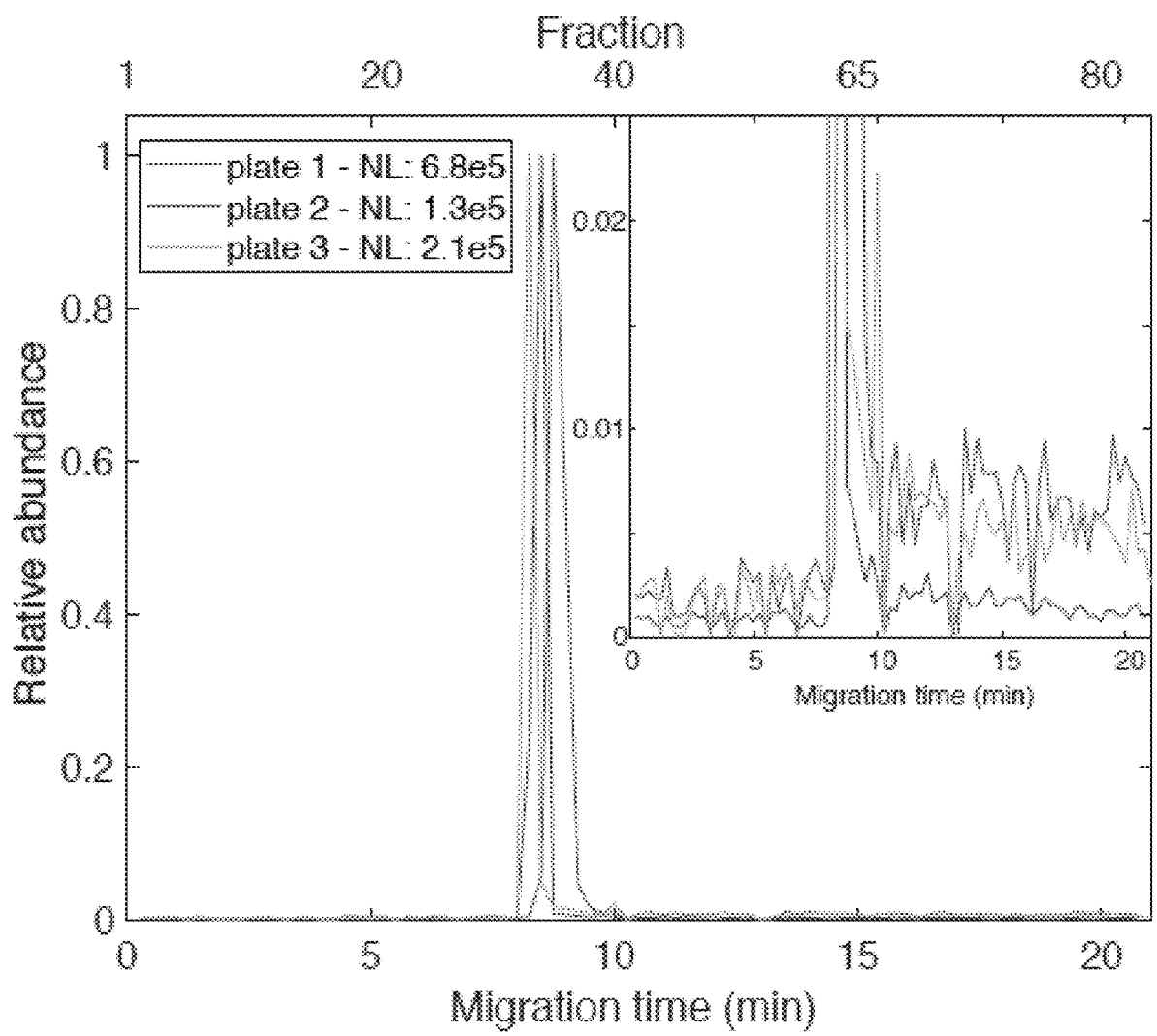
FIG. 4. The total organism electropherograms (TOE) run in triplicate and generated using real-time PCR. Fractionated microbes from an environmental microbiota, produced by separating and collecting fractions into a 96-well microtiter plate, were subjected to amplification across the V4-5 region of the 16S rRNA sequence. Normalization level (NL) is defined as the number of organisms estimated to be present at the peak maximum.
Figure 5:
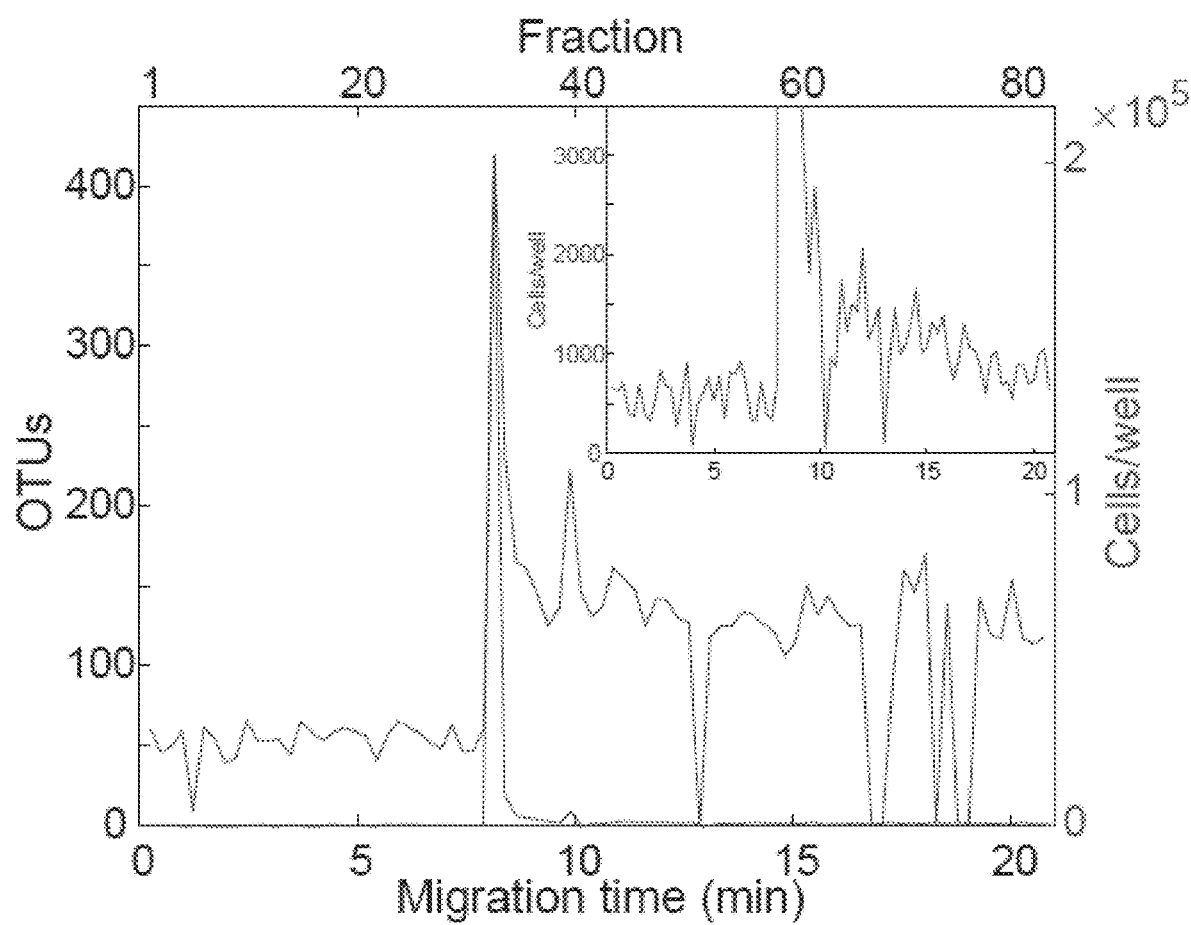
FIG. 5. A graph of the number OTUs mapped to known 16S rRNA sequences per well of the fractionated sample (top trace), along with the TOE (bottom trace) for plate 3 in FIG. 4. The insert presents an expanded view of the TOE.

Example 4. Next-Generation Sequencing of 16s rRNA of Microbes from the Environmental Microbiome—OTU Electropherograms and Bar-Charts After 40 cycles of amplification using real-time PCR to generate the data of FIG. 4, the plates were sequenced. The forward and reverse reads were returned and were about 300 bp in length. Sequences were clustered into OTUs based on similarity and mapped to a microbial genome database; 228 OTUs were observed for the unfractionated sample and a total of 660 OTUs was observed for the fractionated sample. FIG. 5 presents the number of OTUs as a function of migration time (this is referred to as an OTU electropherogram) along with the TOE.

Roughly 50 OTUs were observed per well for the first seven minutes (wells 1-35). The OTU count jumped to ~420 in coincidence with the spike in total cells observed per well for well 33. The number of OTUs decayed to ~100/well by the end of the run.

Figure 6:
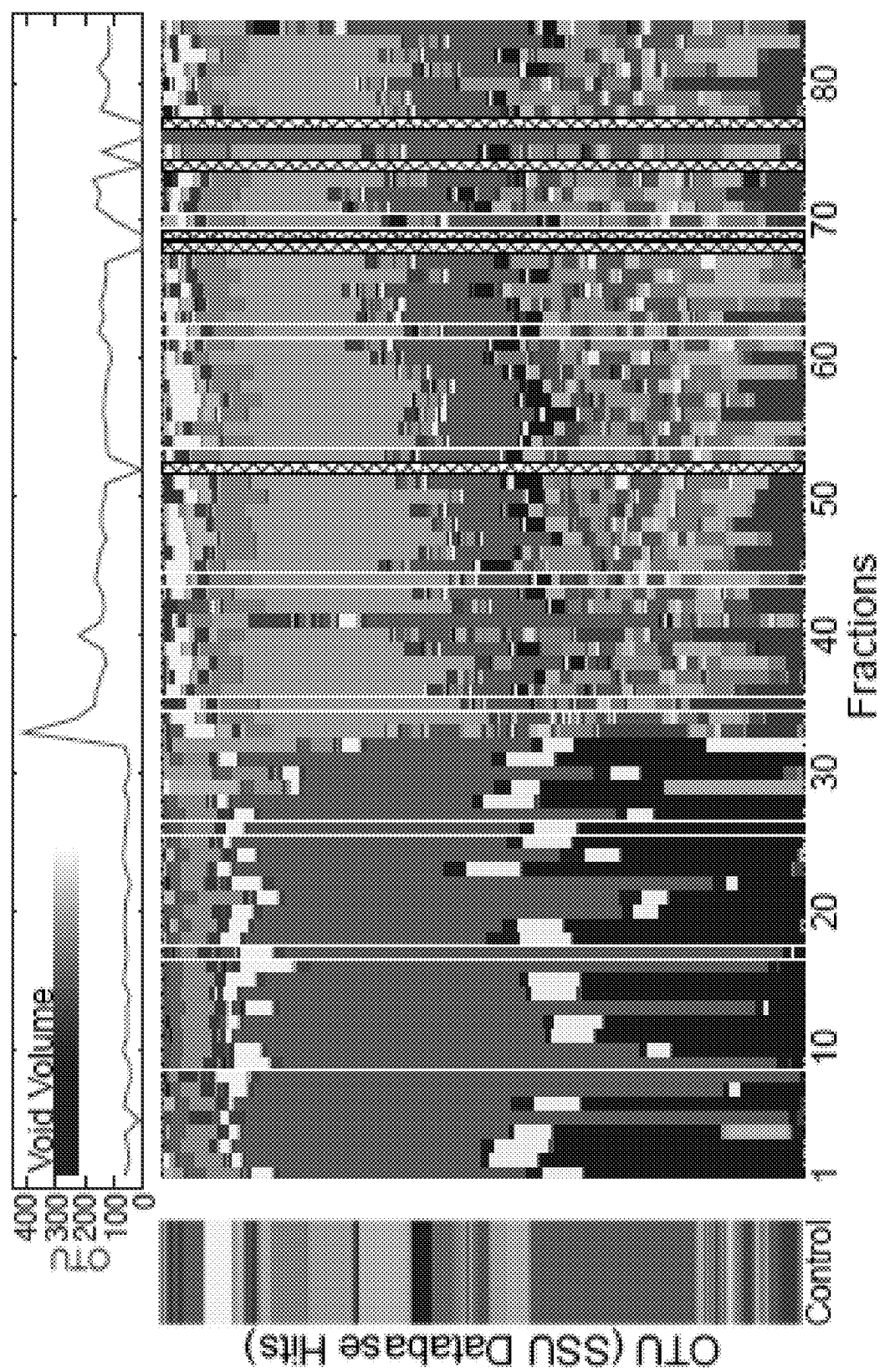
FIG. 6. A bar graph presenting the Qiime readout of next-generation sequencing across the V4-5 region of the 16S rRNA gene for an environmental microbiome. OTUs represented in this chart are restricted to known matches (97% or greater) within the GreenGenes database. The taxonomic assignments for the OTUs are ordered alphabetically and divided by color-coded bars. The size of the bar is proportional to the number of sequences observed for each taxonomic unit. The left graph (control) corresponds to the unfractionated microbiome that generated 228 OTUs. The readout for the 84 fractions is shown on the right a total of 660 OTUs were observed. The top graph presents the OTU electropherogram from FIG. 5

FIG. 6 presents color-coded bar charts where the size of each bar is proportional to the number of sequences observed per OTU. The left panel of FIG. 6 presents data for the unfractionated sample. Roughly 25% of the sequences map to organisms in the Comamonadaceae family, but with no genus or species information. A rare species, such as Clostridium perfringens, was present in 0.01% of the sequences. The right panel of FIG. 6 presents the OTUs for the fractionated sample. Reduced complexity is observed across fractions in comparison to the control. There are two distinct populations in the fractionated samples: fractions 1-32, which are the least complex and dominated by Comamonadaceae, and fractions 33-end, which vary in complexity. The first 35 fractions represent the void volume for the separation and reflect the time necessary for the fastest migrating components to reach the distal end of the capillary. The small number of OTUs in the void volume, and their consistent makeup in those wells, suggests that they arise from contamination of reagents.

The bar graphs following fraction 35 are much more complex and reflect the successful fractionation of the microbiota based on the organisms' electrophoretic properties. 660 OTUs were generated from the fractionated sample.

Example 5. Selected OTU Electropherograms (SOEs)

Figure 7:
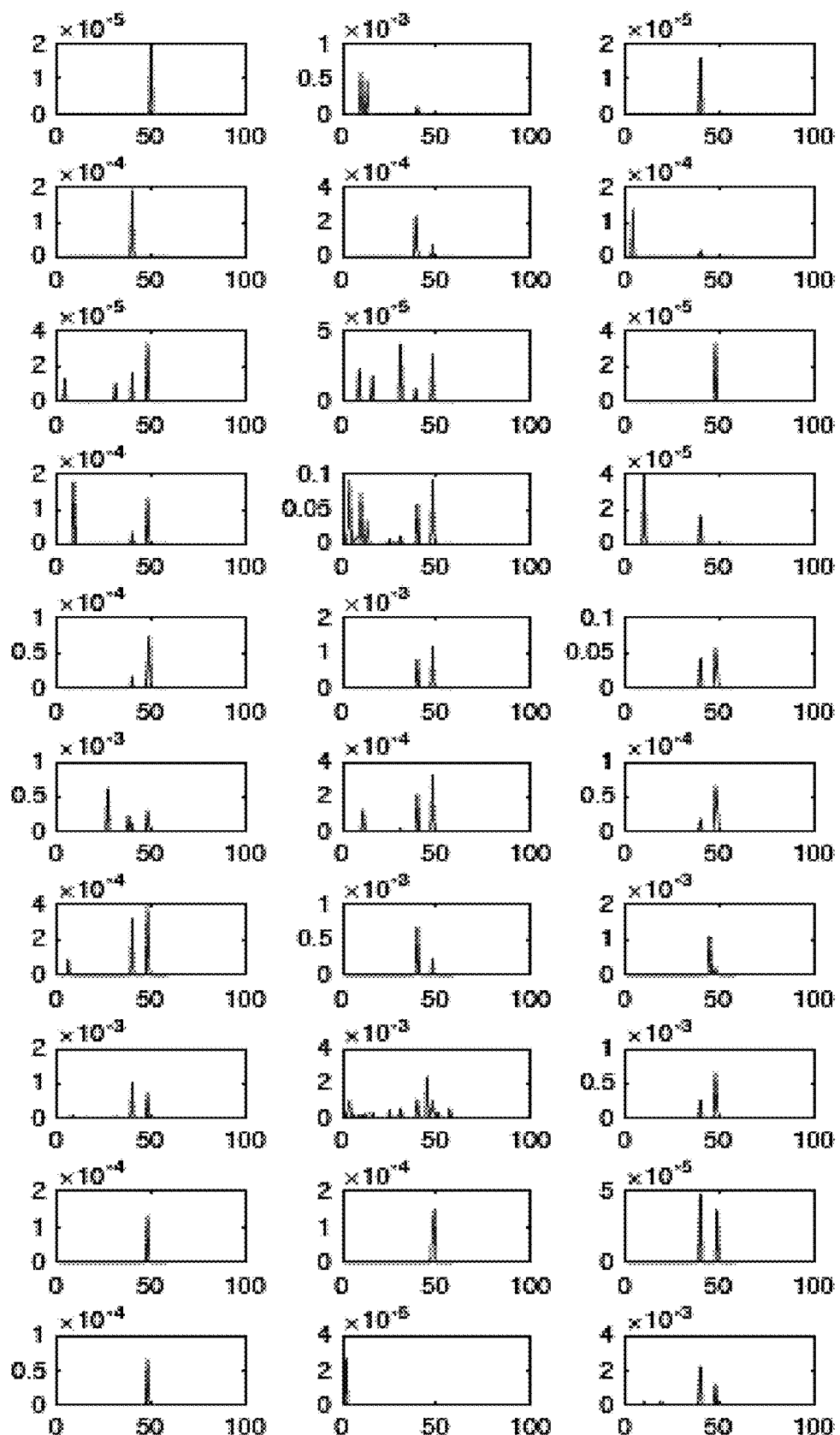
FIG. 7. A series of selected OTU electropherograms. The number of times each OTU was observed per well is plotted against migration time. These results demonstrate that a group of microorganisms with high sequence similarity in the 16S rRNA V4-5 region migrate in a discrete band (single peak). Also, microorganisms with high sequence similarity in the 16S rRNA V4-5 region may possess distinct sizes and/or charges that grant unique electrophoretic mobility despite close genetic relation (i.e. strain level separation, multiple peaks). The methods disclosed herein permit a user to resolve bacteria or other microorganisms even if they are unknown/uncharacterized at the time of separation. Unknown species also resolve into distinct fractions.
Figure 7:
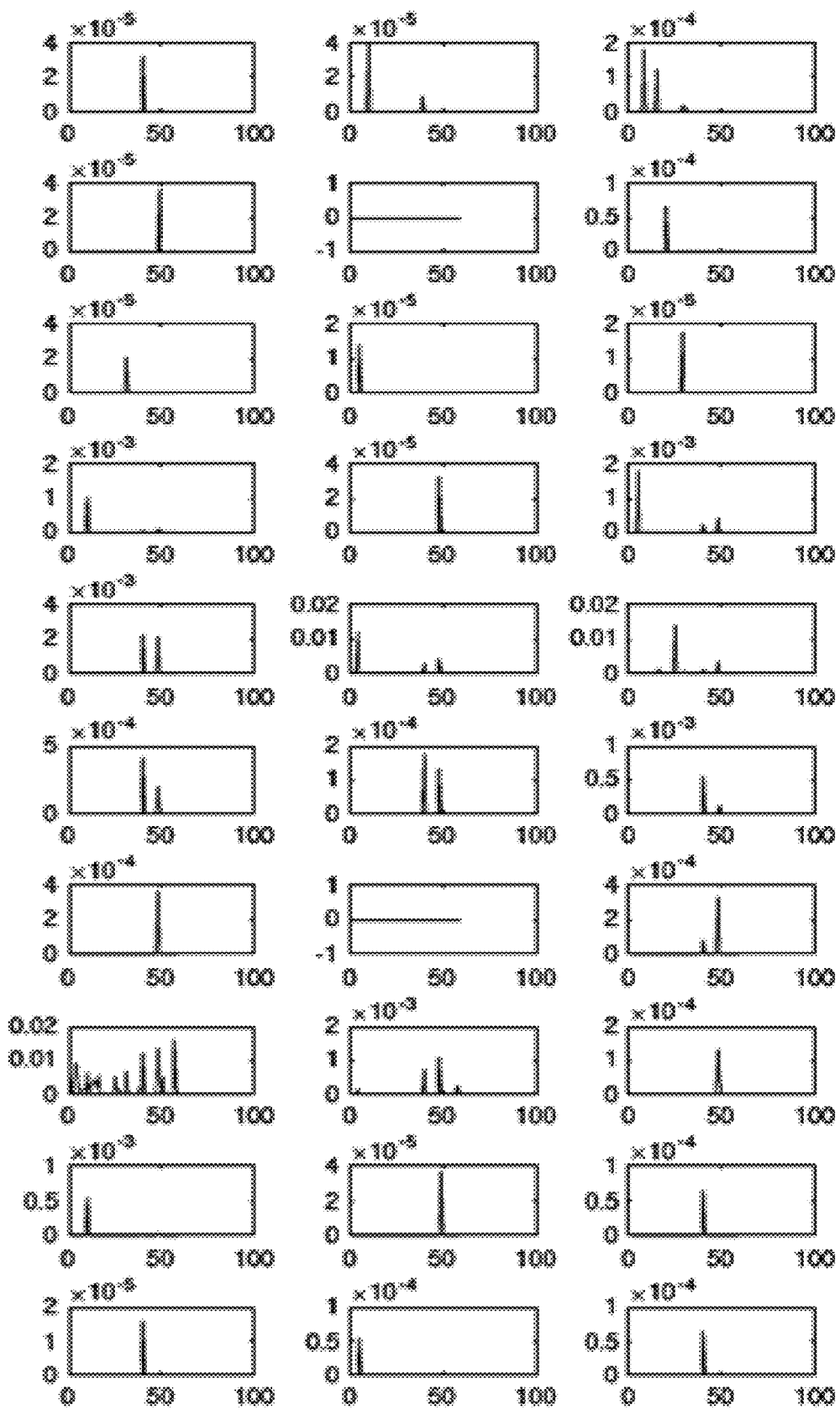
Figure 7:
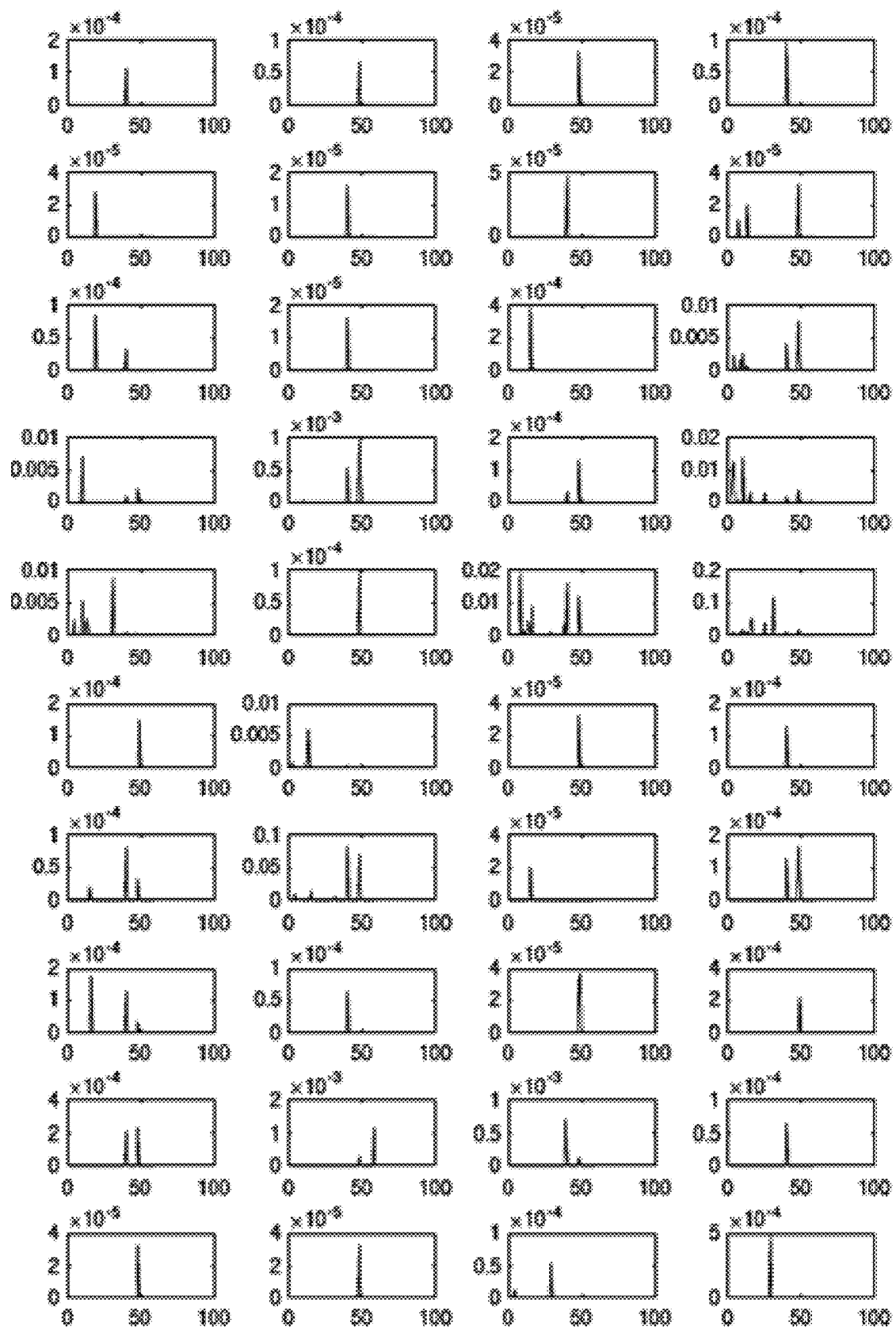

Six hundred sixty (660) selected OTU electropherograms (SOEs) were generated from the fractionated dataset by plotting the number of times each OTU was observed as a function of time (fraction number in time series); SOEs are named by analogy with Selected Ion Electropherograms when using mass spectrometry detection in capillary electrophoresis. A representative set of SOEs is presented in FIG. 7. The plots show very sharp and distinct features for many OTUs. These results indicate that a large portion of the microbiota possess distinct sizes and/or charges within a group of closely related species that grant different electrophoretic mobility to these subgroups within the complex community. It is likely that a number of species have similar 16S rRNA sequences but different electrophoretic properties, generating complex SOEs. Further, these results indicate that the methods disclosed herein permit the identification of numerous species of microbiota that may be undetectable by previous methods (e.g., one order of magnitude greater than other certain methods). This is due to, at least in part, that previous methods of analyzing microbiomes require culturing of each separated fraction in order to perform biochemical or genetic analysis. Also, previous methods of analyzing microbiomes may require a priori knowledge of certain cell surface markers to sort a microbiome into separate fractions (e.g., using flow cytometry) or require incorporation of a detection agent into the sample prior to separation. The present methods overcome these obstacles through direct genetic sequencing of microbes in a fractionated sample without the need to amplify the fractioned microbe in growth medium or the need to detect surface markers for identification of microbes in a fraction.

Example 6. Preparative Continuous Electrophoretic Fractionation of Bacteriophage from Mixed Microbiomes Bacteriophages play an outsized role in environmental and human health. Metagenomics are restricted by an inability to isolate and identify specific components in a microbiota rare, and closely related species. This and dominance of abundant species are some of the major obstacles to progress in the field. Considering the astronomical number of assumed viral species ($\sim 10^{31}$), it is not surprising that unknown sequences dominate virome data. Rapid isolation, characterization, and host-speciation of bacteriophage are essential for the logarithmic expansion of effort necessary to characterize the most abundant organism on Earth. Here we developed a continuous capillary-electrophoretic (CE) fractionation that separates intact phages into discreet fractions based on the chemical properties of the intact particle resulting in non-destructive purification of populations from a diverse environmental mixture.

Nanoliter volumes of bacteriophage suspensions are pneumatically injected into a fused silica capillary for separation. Bacteriophages migrate toward the distal end of the capillary where they are mixed with deposition buffer and pneumatically deposited onto a collection plate. In CE, the conditions of the separation can be modified to influence the mobility of a particular analyte. Innovative techniques were developed to provide conditions for the isolation of both $E.$ $coli$ specific bacteriophage and mixed microorganisms from primary sewage effluent. The data obtained from the innovations established three principal findings:
1.) In mixed microbiome populations, we achieve complete isolation of viral populations from bacterial species.
2.) Modification of electrophoretic conditions produces bacteriophage enriched to near homogeneity, reducing traditional manual plating/isolation.
3.) Phage fractions collected directly onto electron microscopy grids facilitate morphological classification and help define the molecular basis for migration.

These data illustrate that intact phage populations can be fractionated for subsequent detection or offline use. The combination of separation and TEM imaging of intact viruses will be highly beneficial for characterization of novel organisms.

Methods and Results
Microbial Separation by CZE:

Capillary zone electrophoresis (CZE) is an electrophoretic technique capable of extremely high resolution, which separates analytes based on size-to-charge ratio. For mixed microbial samples, separation of intact organisms results in isolation, and consequential enrichment, of individual species. As a result, CZE based separations of microbial populations enables identification and assembly of distinct genomes from closely related species and detection of low-frequency heterologous traits within a single population.

Figure 9:
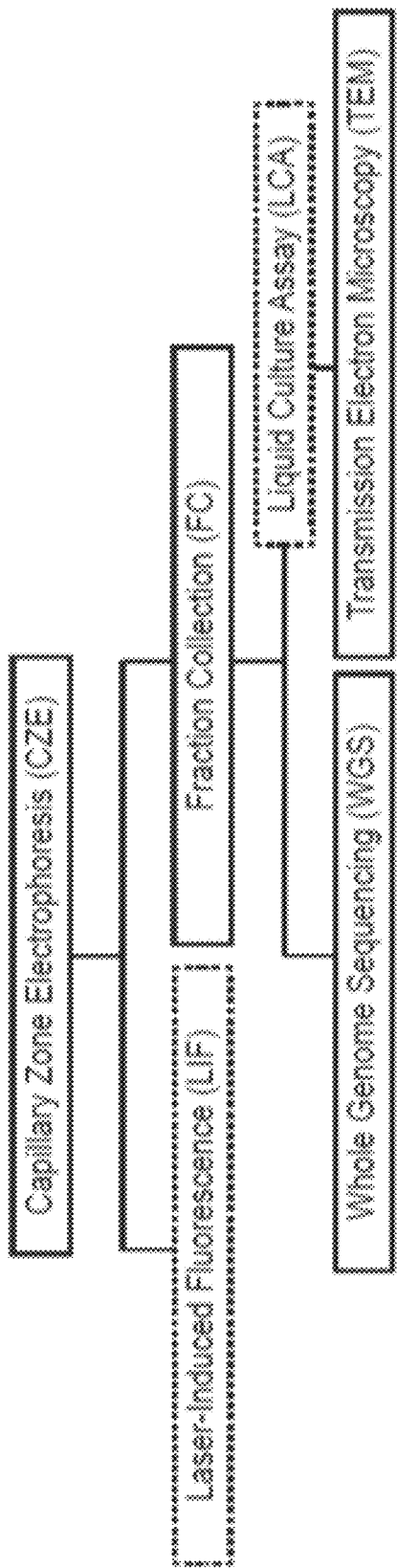
FIG. 9. A flow chart of continuous capillary zone electrophoresis and downstream analysis of microbiota. Complex microbiota are injected intact and separated via CZE; diluted with buffer and isolated to wells of a microtiter plate for analysis. Separation and analyses are diagrammed in the workflow. Separation efficiency and fractionation parameters can be defined using CZE-LIF. Preparative CZE with fraction collection (CZE-FC) is then used to generate separated fractions for on and offline analysis including, for example, uncultured whole genome sequencing (WGS) (FIG. 10), liquid/solid culture assay (LCA) (FIG. 11), or imaging (TEM) (FIG. 12).
Figure 10:
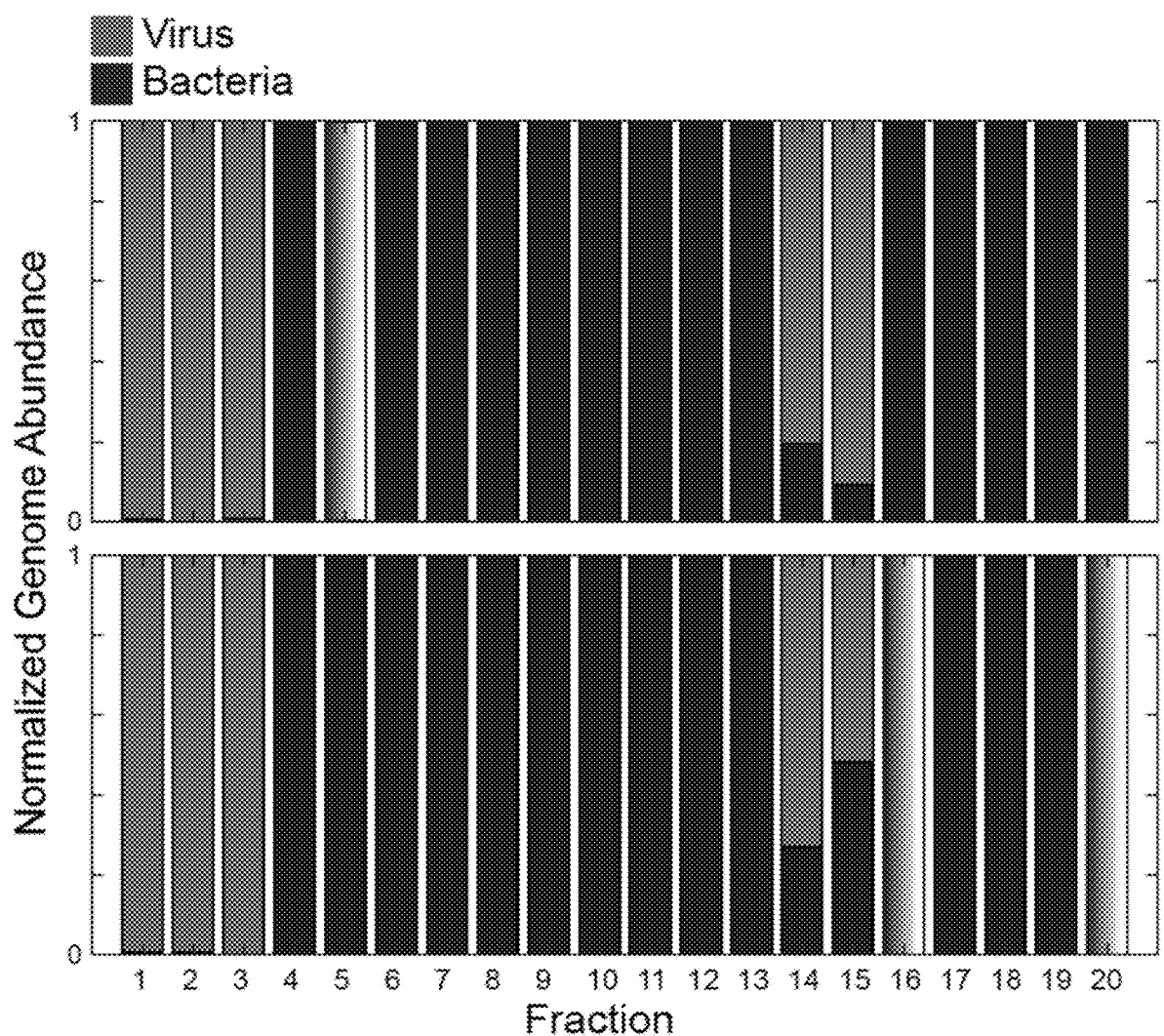
FIG. 10. Viral and bacterial meta-populations are isolated via CZE (CZE-FC-WGS) from a sewage microbiota.

We sampled an environmental microbiome from the Mishawaka, Ind. wastewater treatment plant. Bacterial cells were isolated by centrifugation, washed, and subjected to CZE-FC-WGS (FIGS. 9, 10). Total viruses were isolated from supernatant for virome-specific method optimization. Mixed coliphage were generated by dilution of filtered supernatant in 3×LB, mixed with MG1655+$Mg^{2+}$+$Ca^{2+}$, grown overnight, and lysed with $CHCl_3$. CZE conditions were modified to optimize separation and resolution from this solution of mixed coliphage particles. Fractionation parameters were first defined using CZE-LIF. Preparative CZE-FC was tested with two offline analyses: (1) Fractions were deposited into microtiter plates and inoculated with $E.$ $coli$ MG1655 in LB broth+$Mg^{2+}$+$Ca^{2+}$ for LCA, and (2) Fractions were sampled and imaged for TEM.

As shown in FIG. 10, parameters and DNA isolation were optimized for bacteria. Normalized genome abundance per fraction is plotted for duplicate fractionation runs. Abundant viral DNA was detected almost exclusively in fractions 1-3, with a subset detected in fractions 14-15. Rslunavirus and Pbunavirus were reconstructed in fractions 1-3. Pbunavirus was also isolated in fractions 14-15. The shift indicates differential co-migration, presumably due to co-localization with the bacterial host or an unmapped lysogen. Separation: 15 minutes at 233 V/cm; Background electrolyte: 10 mM Tris-HCl (pH 7.5).

Figure 11:
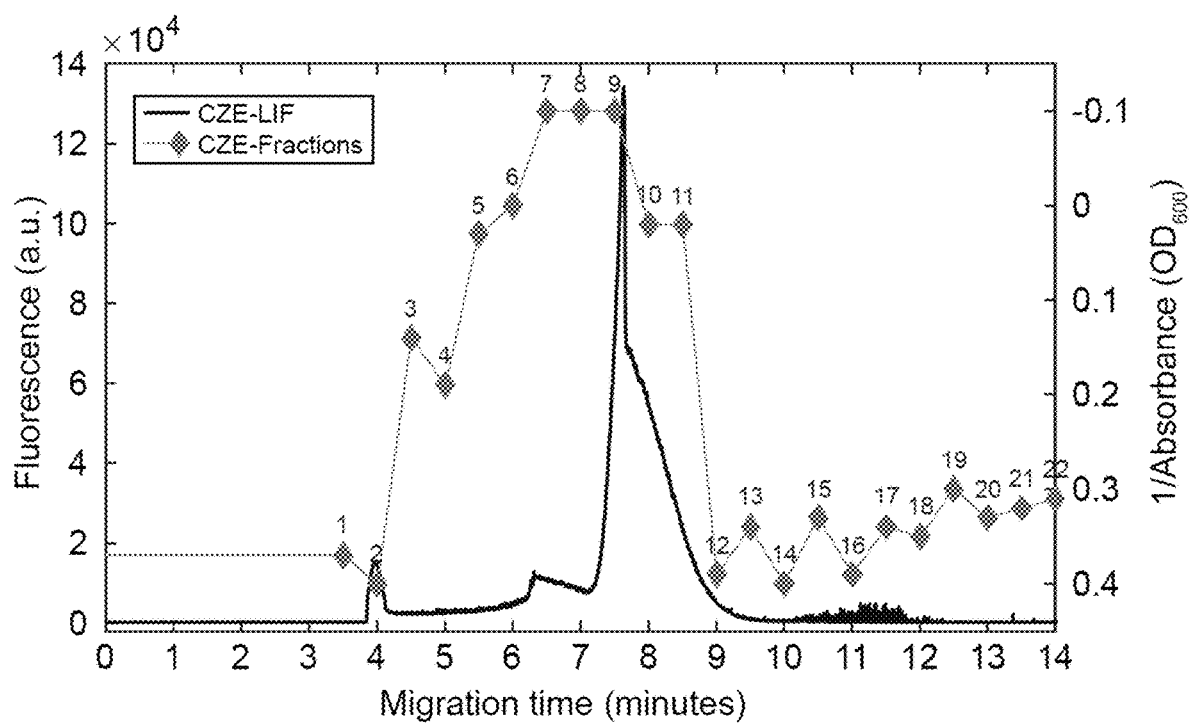
FIG. 11. CZE-LIF and CZE-FC-LCA of a reduced complexity sewage virome.

FIG. 11 presents mixed coliphage isolates stained with SYBR Gold for separation and detection by LIF (trace). In parallel to CZE-LIF, mixed coliphage isolates were separated and collected (FC) for detection in LCA (diamonds): fractionated phage were deposited into microtiter plates and inoculated with $E.$ $coli$ in LB broth, and incubated at 37° C. $OD_{600}$ was monitored for 3 hrs to measure lysis. $1/OD_{600}$ from this liquid culture assay is plotted against fluorescence. Based on the coincidence between measured lysis and fluorescence, we conclude that the SYBR stain does not significantly alter migration time, and fluorescent signal intensity can be interpreted as bacteriophage concentration. Separation: 300V/cm; Background electrolyte: 25 mM Borate (pH 8.3).

Figure 12:
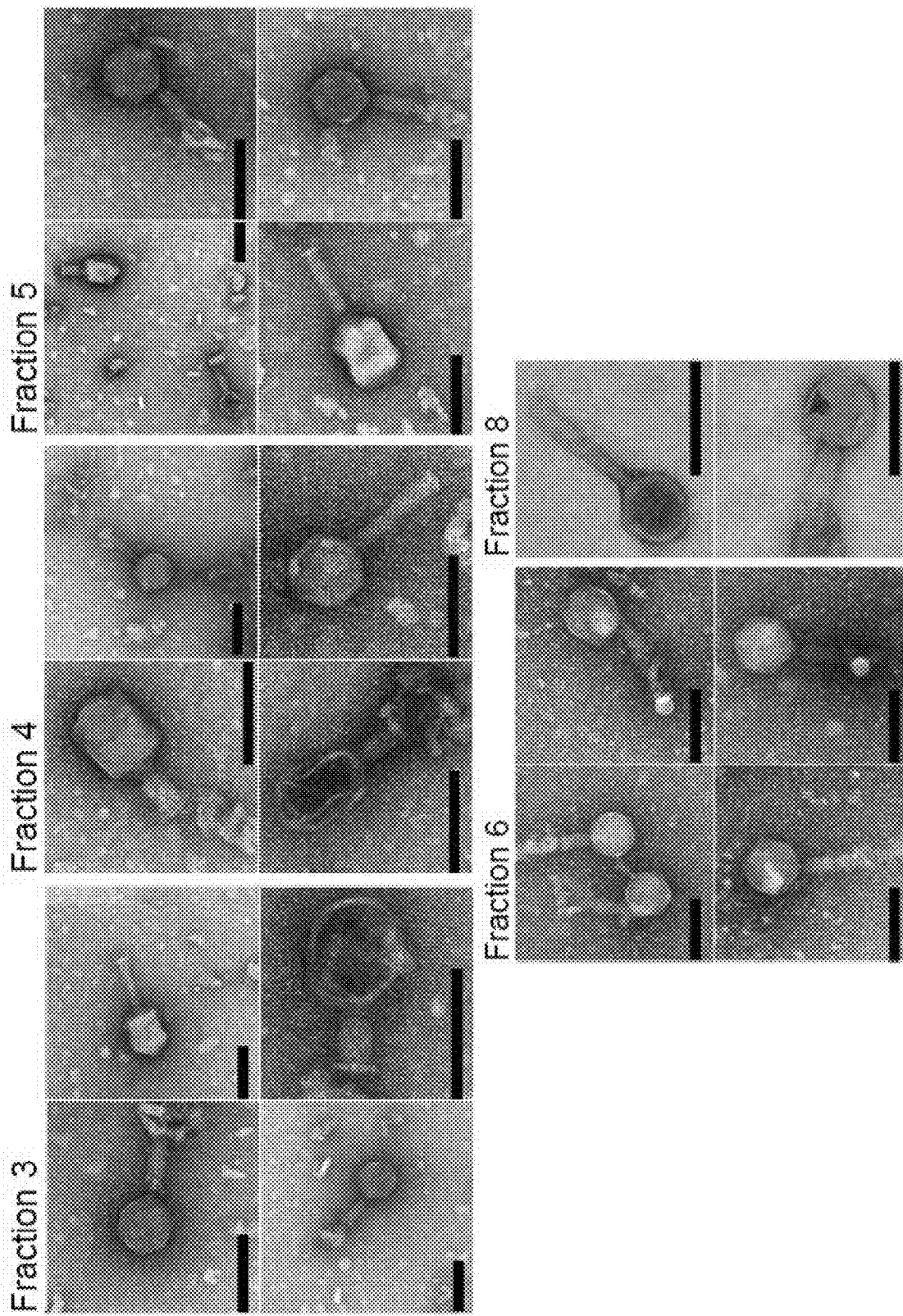
FIG. 12. Transmission Electron Microscopy of fractionated sewage virome.
Figure 12:
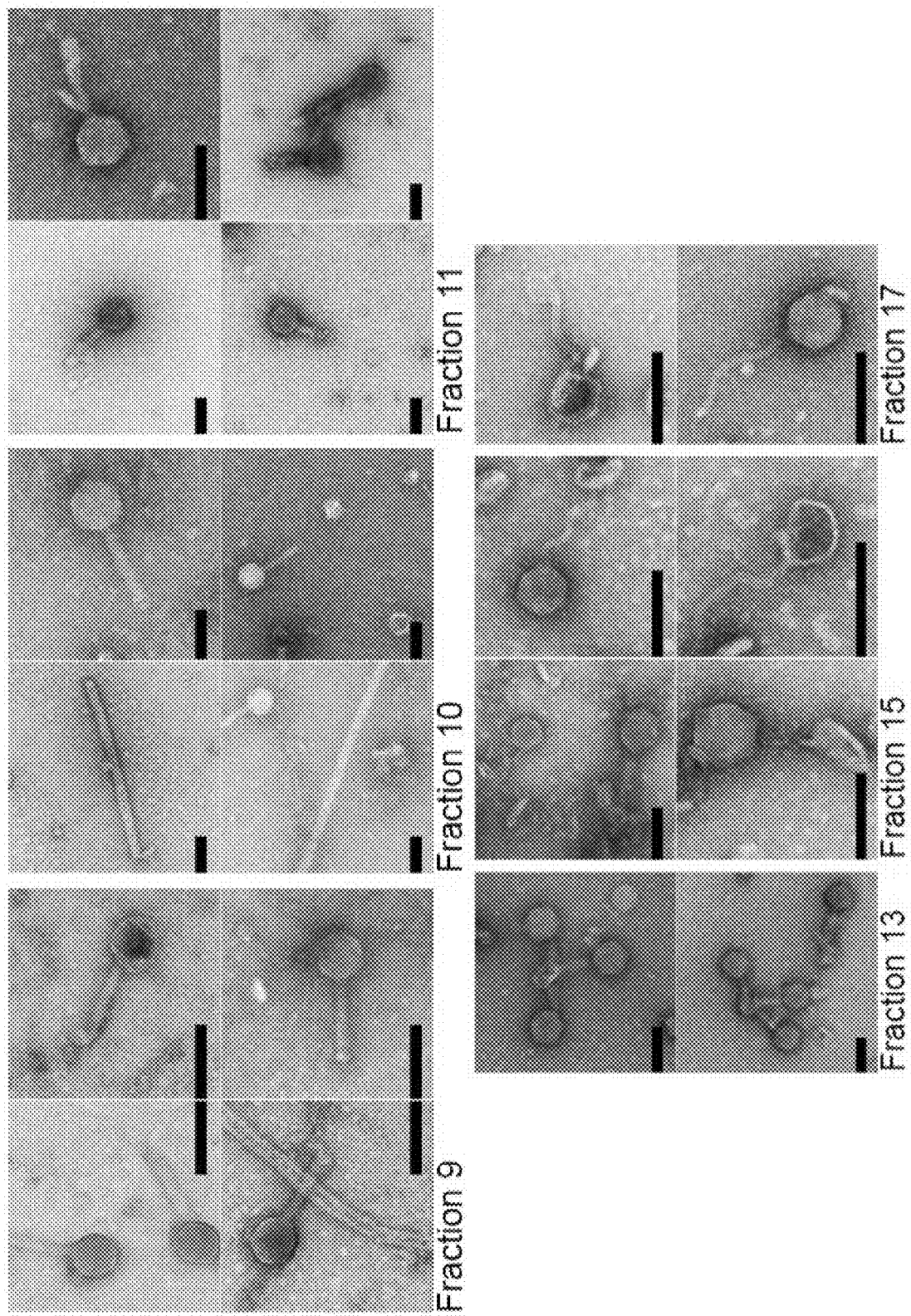

FIG. 12 presents samples negatively stained (2% UA) and imaged at 80 kV using JEOL 2011 transmission electron microscope (bar=100 nm). Shown here are representative images of observed bacteriophage in collected fractions (FIG. 11, LCA). Fractions 1 and 2 contained no observable phage. Distinct morphologies of bacteriophage are present in separate fractions. Early fractions (e.g. 4) contain short T-like phage (Myoviridae) which transition to Lambda-like phage in fractions 8-10 (Siphioviridae). Despite the use of chloroform, filamentous phage (Inoviridae), other members of Myoviridae, and possibly Podoviridae migrate in later fractions (>9). Depending on the class of viruses (e.g., enveloped viruses, non-enveloped viruses), certain detergents and/or dispersants may damage the viruses and should be avoided. For example, sodium dodecyl sulfate (SDS) and Triton X-100 can destroy the viral envelope. Thus, the use of such detergents should be avoided when attempting to fractionate and analyze enveloped viruses according to the methods described herein.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of analyzing a virus or bacteriophage microbiome comprising:
   a) providing a device comprising:
      a separation capillary for an intact virus or bacteriophage microbiota having both a distal and a proximal end, wherein the proximal end of the capillary is in fluidic connection with an injection block that is configured for a sample of the intact virus or bacteriophage microbiota;
      a power source configured to supply a voltage across the separation capillary;
      a background buffer comprising one or more electrolytes wherein the background buffer includes a pH of about 3 to about 11;
      a dispensing valve in fluidic connection to a deposition buffer container;
      a nozzle in fluidic connection to the dispensing valve and the distal end of the capillary through a tee fitting;
      a fraction collector comprising a collector plate connected to a movable stage that is below an open end of the nozzle when collecting fractions; and
      a nucleic acid sequencer interfaced with the fraction collector;
      wherein the sample of intact virus or bacteriophage microbiota is separated by the separation capillary;
   b) inserting a sample comprising a mixture of virus or bacteriophage microbiota into the injection block;
   c) applying a constant voltage to the separation capillary to separate the sample into fractions;
   d) pressurizing the deposition buffer container, wherein the deposition buffer container comprises a deposition buffer;
   e) opening the dispensing valve;
   f) collecting the fractions of purified intact virus or bacteriophage microbiota that have been separated from other microbiota in the mixture;
   g) optionally amplifying the purified virus or bacteriophage microbiota;
   h) visualizing the fractionated virus or bacteriophage via electron microscopy; and
   h) sequencing nucleic acid of the fractionated virus or bacteriophage using the nucleic acid sequencer;
   wherein a microbiome within a fraction is analyzed from the fractionated virus or bacteriophage microbiota by nucleic acid sequencing.

2. The method of claim 1 wherein the electrolyte is borate present in the background buffer at a concentration of about 10 mM to about 100 mM.

3. The method of claim 1 wherein the voltage applied to the separation capillary is about 250 V/cm to about 350 V/cm.

4. The method of claim 1 wherein the dispensing valve opens when fractions are collected.

5. The method of claim 1 wherein the injection block comprises the sample and a sample buffer.

6. The method of claim 5 wherein the sample buffer and the deposition buffer are chemically similar.

7. The method of claim 1 wherein the fraction collector comprises a microtiter plate, a Petri dish, or a combination thereof.

8. The method of claim 7 wherein the Petri dish comprises a host cell on or in a cell growth medium.

9. The method of claim 7 wherein the microtiter plate comprises a series of wells, and wherein at least one well comprises a lysis reagent mixture for conducting a polymerase chain reaction.

* * * * *